United States Patent [19]

Noda

[11] Patent Number: 5,489,470

[45] Date of Patent: Feb. 6, 1996

[54] BIODEGRADABLE COPOLYMERS AND PLASTIC ARTICLES COMPRISING BIODEGRADABLE COPOLYMERS

[75] Inventor: Isao Noda, Fairfield, Ohio

[73] Assignee: The Procter & Gamble Company, Cincinnati, Ohio

[21] Appl. No.: 422,009

[22] Filed: Apr. 13, 1995

Related U.S. Application Data

[60] Continuation of Ser. No. 364,917, Dec. 28, 1994, which is a division of Ser. No. 306,349, Sep. 15, 1994, abandoned, which is a division of Ser. No. 247,539, May 23, 1994, abandoned, and a continuation-in-part of Ser. No. 247,539, which is a continuation of Ser. No. 187,969, Jan. 28, 1994, abandoned.

[51] Int. Cl.[6] ............................. B32B 27/00; A61F 13/15
[52] U.S. Cl. ....................... 428/286; 428/284; 428/913; 604/358
[58] Field of Search ..................... 428/284, 286, 428/913; 604/358

[56] References Cited

U.S. PATENT DOCUMENTS

| | | | |
|---|---|---|---|
| 4,393,167 | 7/1983 | Holmes et al. | 525/64 |
| 4,477,654 | 10/1984 | Holmes et al. | 528/361 |
| 4,603,070 | 7/1986 | Steel et al. | 428/88 |
| 4,880,592 | 11/1989 | Martini et al. | 264/514 |
| 5,004,664 | 4/1991 | Fuller et al. | 430/106.6 |
| 5,023,316 | 6/1991 | Benvenuti et al. | 528/357 |
| 5,135,859 | 8/1992 | Witholt et al. | 435/135 |
| 5,135,966 | 8/1992 | Chatterjee et al. | 523/126 |
| 5,191,016 | 3/1993 | Yalpani | 525/54.2 |
| 5,191,037 | 3/1993 | Doi et al. | 525/450 |
| 5,231,148 | 7/1993 | Kleinke et al. | 525/450 |
| 5,391,423 | 2/1995 | Wnuk et al. | 428/217 |

FOREIGN PATENT DOCUMENTS

| | | | |
|---|---|---|---|
| 0400855 | 5/1990 | European Pat. Off. | C08K 5/53 |
| 0416624A2 | 3/1991 | European Pat. Off. | C08G 63/682 |
| 0533144A2 | 3/1993 | European Pat. Off. | C12P 7/62 |
| 0540182A3 | 5/1993 | European Pat. Off. | C08L 67/04 |
| 0540182A2 | 5/1993 | European Pat. Off. | C08L 67/04 |
| 0560014A1 | 9/1993 | European Pat. Off. | A61L 25/00 |
| 2909145 | 6/1991 | Germany | C12P 7/42 |
| 4040158A1 | 6/1992 | Germany | C09D 167/04 |
| 4212801A1 | 11/1992 | Germany | A61K 6/087 |
| 3-277656 | 12/1991 | Japan | C08L 67/04 |
| 4-89004 | 3/1992 | Japan | A45C 11/18 |
| 04136067-A | 11/1992 | Japan | C08L 67/04 |
| 04136066-A | 11/1992 | Japan | C08L 67/04 |
| 05017590-A | 1/1993 | Japan | C08J 5/00 |
| 05034343 | 2/1993 | Japan | G01N 33/52 |
| 05093318-A | 4/1993 | Japan | D01F 8/14 |
| 05093317-A | 4/1993 | Japan | D01F 8/14 |
| 05230351-A | 9/1993 | Japan | C08L 67/02 |
| 91/13207 | 9/1991 | WIPO | D21H 19/62 |
| 91/18994 | 12/1991 | WIPO | C12P 7/62 |
| 92/09211 | 6/1992 | WIPO | A23L 1/29 |
| 92/09210 | 6/1992 | WIPO | A23L 1/221 |
| 92/18553 | 10/1992 | WIPO | C08G 63/06 |
| 92/19747 | 11/1992 | WIPO | C12N 15/82 |
| 92/21708A1 | 12/1992 | WIPO | C08G 63/06 |
| 93/02194 | 2/1993 | WIPO | C12N 15/52 |

OTHER PUBLICATIONS

Abe, H. Y. Doi, T. Fukushima and H. Eya, "Biosynthesis From Gluconate of a Random Copolyester Consisting of 3–hydroxy–butyrate and medium–chain–length 3–hydroxyalkanoates by Pseudomonas sp. 61–3", *Int. J. Biol. Macromol.*, vol. 16, No. 3, (May/Jun. 1994).

Agostini, D. E., J. B. Lando & J. R. Shelton, "Synthesis and Characterization of Poly–β–hydroxybutyrate. I. Synthesis of Crystalline DL–poly–β–hydroxybutyrate from DL–β–butyrolactone", *Journal of Polymer Science*, Part A–1, vol. 9, No. 10, pp. 2775–2787 (Oct. 1971).

Aida, T., Y. Maekawa, S. Asano and S. Inoue, "Immortal Polymerization. Polymerization of Epoxide and β–Lactone with Aluminum Porphyrin in the Presence of Protic Compound", *Macromolecules*, vol. 21, No. 5, pp. 1195–1202 (May 1988).

Amos, D. A. & M. J. McInerney, "Composition of Poly–β–hydroxyalkanoate From *Syntrophomonas wolfei* Grown on Unsaturated Fatty Acid Substrates", *Arch. Microbiol.*, vol. 155, No. 2, pp. 103–106 (Mar. 1991).

Anderson, A. J., G. W. Haywood, D. R. Williams & E. A. Dawes, "The Production of Polyhydroxyalkanoates From Unrelated Carbon Sources", *Novel Biodegradable Microbial Polymers*, Dawes, E. A. Ed., Kluwer Academic Publ., Boston, pp. 119–129, (1990) (NATO ASI Series E. Applied Sciences–vol. 186).

(List continued on next page.)

Primary Examiner—Morton Foelak
Attorney, Agent, or Firm—Brahm J. Corstanje; David L. Suter; Jacobus C. Rasser

[57] ABSTRACT

The present invention relates to biodegradable PHA copolymers comprising at least two randomly repeating monomer units. The present invention further relates to a plastic article comprising a biodegradable copolymer, wherein the biodegradable copolymer comprises at least two randomly repeating monomer units (RRMU) wherein the first RRMU has the structure

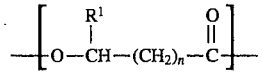

wherein $R^1$ is H, or $C_1$ or $C_2$ alkyl, and n is 1 or 2; the second RRMU has the structure

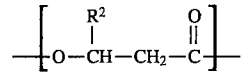

wherein $R^2$ is a $C_4$–$C_{19}$ alkyl or alkenyl; and wherein at least 50% of the RRMUs have the structure of the first RRMU. The present invention further relates to an absorbent article comprising a liquid pervious topsheet, a liquid impervious backsheet comprising a film comprising a PHA of the present invention and an absorbent core positioned between the topsheet and the backsheet.

5 Claims, No Drawings

OTHER PUBLICATIONS

Anderson, A. J. & E. A. Dawes, "Occurrence, Metabolism, Metabolic Role, and Industrial Uses of Bacterial Polyhydroxyalkanoates", *Microbiological Reviews*, vol. 54, No. 4, pp. 450–472 (Dec. 1990).

Bero, M., J. Kasperczyk & G. Adamus, "Coordination of Polymerization of Lactides, 3", *Makromol. Chem.*, vol. 194, No. 3, pp. 907–912 (Mar. 1993).

Billingham, N. C., M. G. Proctor & J. D. Smith, "Polymerization and Copolymerization of β–butyrolactone by Aluminum Compounds", *Journal of Organometallic Chemistry*, vol. 341, pp. 83–93 (1988).

Brandl, H., E. J. Knee, Jr., R. C. Fuller, R. A. Gross & R. W. Lenz, "Ability of the Phototrophic Bacterium *Rhodospirillum rubrum* to Produce Various Poly(β–hydroxyalkanoates): Potential Sources for Biodegradable Polyesters", *Int. J. Biol. Macromol.*, vol. 11, pp. 49–54 (Feb. 1989).

"Novel Biodegradable Microbial Polymers", E. A. Dawes, Ed., NATO ASI Series, Series E:Applied Sciences, vol. 186.

Doi, Y. (ed) "Microbial Polyesters", Chapter 1, *VCH Publishers*, New York, pp. 1–9 (1990).

Doi, Y., "Microbial Synthesis, Physical Properties and Biodegradability of Polyhydroxyalkanoates", *Advances in Biopolymer Engineering Conference*, (Jan. 23–28, 1994).

Doi, Y., "Microbial Polyesters", Chapters 3, 4 and 5, *VCH Publishers*, New York, pp. 33–98 (1990).

Dubois, P., I. Barakat, R. Jérôme & P. Teyssié, "Macromolecular Engineering of Polylactones and Polylactides. 12. Study of the Depolymerization Reactions of Poly(ε–caprolactone) with Functional Aluminum Alkoxide End Groups", *Macromolecules*, vol. 26, No. 17, pp. 4407–4412 (Aug. 1993).

Gross, R. A., C. DeMello, R. W. Lenz, H. Brandl & R. C. Fuller, "Biosynthesis and Characterization of Poly(β–hydroxyalkanoates Produced by *Pseudomonas oleovorans*", *Macromolecules*, vol. 22, No. 3, pp. 1106–1115 (Mar. 1989).

Gross, R. A., Y. Zhang, G. Konrad & R. W. Lenz, "Polymerization of β–monosubstituted–β–propiolactones Using Trialkylaluminum–water Catalytic Systems and Polymer Characterization", *Macromolecules*, vol. 21, No. 9, pp. 2657–2668 (Sep. 1988).

Haywood, G. W., A. J. Anderson & E. A. Dawes, "A Survey of the Accumulation of Novel Polyhydroxyalkanoates by Bacteria:", *Biotechnology Letters*, vol. 11, No. 7, pp. 471–476 (1989).

Hocking, P. J. & R. H. Marchessault, "Syndiotactic Poly [(R,S)–β–hydroxybutyrate] Isolated from Methylaluminoxane–catalyzed Polymerization", *Polymer Bulletin*, vol. 30, pp. 163–170 (1993).

Holmes, P. A., "Developments In Crystalline Polymers—2", *D. C. Bassett, Ed., Elsevier Science Publishing Co.*

Hori, Y., M. Suzuki, A. Yamaguchi & T. Nishishita, "Ring–opening Polymerization of Optically Active β–butyrolactone Using Distannoxane Catalysts: Synthesis of High Molecular Weight Poly(3–hydroxybutyrate)", *Macromolecules*, vol. 26, No. 20, pp. 5533–5534 (Sep. 1993).

Inoue, S., Y. Tomoi, T. Tsuruta & J. Furukawa, "Organometallic–catalyzed Polymerization of Propiolactone", (1961).

Kaspercayk, J. & M. Bero, "Coordination Polymerization of lactides, 4", *Makromol. Chem.*, vol. 194, No. 3, pp. 913–925 (Mar. 1993).

Kemnitzer, J. E., S. P. McCarthy & R. A. Gross, "Preparation of Predominantly Syndiotactic Poly(β–hydroxybutyrate) by the Tribytyltin Methoxide Catalized Ring–Opening Polymerization of Racemic β–butyrolactone", *Macromolecules*, vol. 26, No. 6, pp. 1221–1229 (Mar. 1993).

Kobayashi, G. and T. Shiotani, "Biosynthesis and Characterization of Poly(3–hydroxybutyrate–co–hydroxyhexanoate)", *SPSJ 41st Annual Meeting (May 29, 1992)*.

Kumagai, Y. & Y. Doi, "Synthesis of a Block Copolymer of Poly(3–hydroxybutyrate) and Poly(Ethylene Glycol) and Its Application to Biodegradable Polymer Blends", *Journal of Environmental Polymer Degradation*, vol. 1, No. 2, pp. 81–87 (1993).

Lauzier, C. A., C. J. Monasterios, I. Saracovan, R. H. Marchessault and B. A. Ramsay, "Film Formation and Paper Coating with Poly(β–hydroxyalkanoate) a Biodegradable Latex", *TAPPI Journal*, vol. 76, No. 5, pp. 71–77 (May 1993).

Le Borgne, A. & N. Spassky, "Stereoelective Polymerization of β–butyrolactone", *Polymer*, vol. 30, pp. 2312–2319 (Dec. 1989).

"Living Polymerization and Selective End Functionalization of ε–Caprolactone Using Zinc Alkoxides as Initiators", *Macromolecules*, vol. 24, No. 24, pp. 6542–6545 (Nov. 1991).

Liebergesell, M., F. Mayer & A. Steinbuchel, "Analysis of Polyhydroxyalkanoic Acid–biosynthesis Genes of Anoxygenic Phototrophic Bacteria Reveals Synthesis of a Polyester Exhibiting an Unusual Composition", *Applied Microbiology and Biotechnology*, vol. 40, pp. 2–3 (Nov. 1993).

Liebergesell, M., E. Hustede, A. Timm, A. Steinbüchel, R. C. Fuller, R. W. Lenz & H. G. Schlegel, "Formation of Poly(3–hydroxyalkanoates) by Phototrophic and Chemolithotrophic Bacteria", *Arch. Microbiol.*, vol. 155, No. 5, pp. 415–421 (Oct. 1991).

Marchessault, R. H., P. Rioux and I. Saracovan, "Direct Electrostatic Coating of Paper", *Nordic Pulp and Paper Research Journal No. 1*, pp. 211–216 (Apr. 1993).

Müller, H. and D. Seebach, "Poly(hydroxyalkanoates): A Fifth Class of Physiologically Important Organic Bipolymers?", *Angew. Chem. Int. Ed. Engl.*, vol. 32, pp. 477–502 (1993).

Poirier, Y., D. E. Dennis, C. Nawrath & C. Somerville, "Progress Toward Biologically Produced Biodegradable Thermoplastics", *Advanced Materials*, vol. 3, No. 1, pp. 30–36 (1993).

Ramsay, B. A., I. Saracovan, J. A. Ramsay and R. H. Marchessault, "Continuous Production of Long–Side–Chain Poly–β–Hydroxyalkanoates by *Pseudomonas oleovorans*", *Applied and Environmental Microbiology*, vol. 57, No. 3, pp. 625–629 (Mar. 1991).

Shelton, J. R., D. E. Agostini & J. B. Lando, "Synthesis and Characterization of Poly–β–hydroxybutyrate. II. Synthesis of D–poly–β–hydroxybutyrate and the Mechanism of Ring–opening Polymerization of β–butyrolactone", *Journal of Polymer Science*, Part A–1, vol. 9, No. 10, pp. 2789–2799 (Oct. 1971).

Shimamura, E., M. Scandola and Y. Doi, "Microbial Synthesis and Characterization of Poly(3–hydroxybutyrate–co–3–hydroxypropionate)", *Macromolecules*, vol. 27, No. 16, pp. 4429–4435 (Aug. 1, 1994).

Shimamura, E., K. Kasuya, G. Kobayashi, T. Shiotani, Y. Shima and Y. Doi, "Physical Properties and Biodegradability of Microbial Poly (3–hydroxybutyrate–co–3–hydroxyhexanoate)", *Macromol*

*ecules*, vol. 27, No. 3, pp. 878–880 (Jan. 1994).

Steinbüchel & H. G. Schlegel, "Physiology and Molecular Genetics of Poly(β–hydroxyalkanoic acid) Synthesis in *Alcaligenes eutrophus*", *Molecular Microbiology*, vol. 5, No. 3, pp. 535–542 (Mar. 1991).

Tanahashi, N. & Y. Doi, "Thermal Properties and Stereoregularity of Poly(3–hydroxybutyrate) Prepared from Optically Active β–butyrolactone With a Zinc–based Catalyst", *Macromolecules*, vol. 24, No. 20, pp. 5732–5733 (Sep. 1991).

Timm, A. & A. Steinbüchel, "Formation of Polyesters Consisting of Medium–Chain–Length 3–hydroxyalkanoic Acids from Gulconate by *Pseudonomads aeruginosa* and Other Fluorescent Pseudomonads", Applied and Environmental Microbiology, vol. 56, No. 11, pp. 3360–3367 (Nov. 1990).

Timm, A. & A. Steinbüchel, "Formation of Poly(3–hydroxyalkanoates) by Wild Type and Recombinant Strains of *Pseudomonas aeruginosa* and Other Fluorescent Pseudomonods", *Novel Biodegradable Microbial Polymers*, Dawes, E. A., Ed., Kluwer, Academic Publ., Boston, pp. 445–447 (1990) (NATO ASI Series E, Applied Sciences—vol. 186).

Ulmer, H. W., R. A. Gross, M. Posada, P. Weisbach, R. C. Fuller & R. W. Lenz, "Bacterial Production of Poly(β–hydroxyalkanoates) Containing Unsaturated Repeating Units by *Rhodospirillum rubrum*", *Macromolecules*, vol. 27, No. 7, pp. 1675–1679 (Mar. 1994).

Zhang, Y., R. A. Gross & R. W. Lenz, "Stereochemistry of the Ring–opening Polymerization of (S)–β–butyrolactone", *Macromolecules*, vol. 23, No. 13, pp. 3206–3212 (Jun. 1990).

BIODEGRADABLE COPOLYMERS AND PLASTIC ARTICLES COMPRISING BIODEGRADABLE COPOLYMERS

This is a continuation of application Ser. No. 08/364,917, filed on Dec. 28, 1994, which is a divisional of application Ser. No. 08/306,349, filed on Sep. 15, 1994, now abandoned, which is a divisional and continuation-in-part of application Ser. No. 08/247,539, filed on May 23, 1994, now abandoned, which is a continuation of application Ser. No. 08/187,969, filed on Jan. 28, 1994, now abandoned.

TECHNICAL FIELD

The present invention relates to biodegradable copolymers and plastic articles comprising such biodegradable copolymers.

BACKGROUND

Polymers find uses in a variety of plastic articles including films, sheets, fibers, foams, molded articles, adhesives and many other specialty products. For applications in the areas of packaging, agriculture, household goods and personal care products, polymers usually have a short (less than 12 months) use cycle. For example, in food packaging, polymers play the role of a protective agent and are quickly disposed of after the contents are consumed. Household products such as detergent bottles and diapers are immediately discarded once the product is used.

The majority of this plastic material ends up in the solid waste stream, headed for rapidly vanishing and increasingly expensive landfill space. While some efforts at recycling have been made, the nature of polymers and the way they are produced and converted to products limits the number of possible recycling applications. Repeated processing of even pure polymers results in degradation of material and consequently poor mechanical properties. Different grades of chemically similar plastics (e.g., polyethylenes of different molecular weights, as used in milk jugs and grocery sacks) mixed upon collection can cause processing problems that make the reclaimed material inferior or unusable.

Absorbent article applications such as diapers, sanitary napkins, pantiliners and the like, involve several different types of plastics. In these cases, recycling is particularly costly because of the difficulty in separating the different components. Disposable products of this type generally comprise some sort of fluid-permeable topsheet material, an absorbent core, and a fluid-impermeable backsheet material. Heretofore, such absorbent structures have been prepared using, for example, topsheet materials prepared from woven, non-woven, or porous formed-film polyethylene or polypropylene materials. Backsheet materials typically comprise flexible polyethylene sheets. Absorbent core materials typically comprise wood pulp fibers or wood pulp fibers in combination with absorbent gelling materials. Although such products largely comprise materials which would be expected ultimately to degrade, and although products of this type contribute only a very small percentage of the total solid waste materials generated by consumers each year, nevertheless, there is currently a perceived need to devise such disposable products from materials which are compostable.

A conventional disposable absorbent product is already to a large extent compostable. A typical disposable diaper, for example, consists of about 80% of compostable materials, e.g., wood pulp fibers, and the like. In the composting process soiled disposable absorbent articles are shredded and commingled with organic waste prior to the composting per se. After composting is complete, the non-compostable particles are screened out. In this manner even today's absorbent articles can successfully be processed in commercial composting plants.

Nevertheless, there is a need for reducing the amount of non-compostable materials in disposable absorbent articles. There is a particular need to replace polyethylene backsheets in absorbent articles with liquid impervious films of compostable material, because the backsheet is typically one of the largest non-compostable components of a conventional disposable absorbent article.

In addition to being compostable, the films employed as backsheets for absorbent articles must satisfy many other performance requirements. For example, the resins should be thermoplastic such that conventional film processing methods can be employed. These methods include cast film and blown film extrusion of single layer structures and cast or blown film coextrusion of multilayer structures. Other methods include extrusion coating of one material on one or both sides of a compostable substrate such as another film, a non-woven fabric, or a paper web.

Still other properties are essential in product converting operations where the films are used to fabricate absorbent articles. Properties such as tensile strength, tensile modulus, tear strength, and thermal softening point determine to a large extent how well a film will run on converting lines.

In addition to the aforementioned properties, still other properties are needed to meet the end user requirements of the absorbent article. Film properties such as impact strength, puncture strength, and moisture transmission are important since they influence the absorbent article's durability and containment while being worn.

Once the absorbent article is disposed of and enters a composting process, other properties become important. Regardless of whether incoming waste is preshredded or not, it is important that the film or large film fragments undergo an initial breakup to much smaller particles during the initial stages of composting. Otherwise, the films or large fragments may be screened out of the compost stream and may never become part of the final compost.

In the past, the biodegradability and physical properties of a variety of polyhydroxyalkanoates have been studied. Polyhydroxyalkanoates are polyester compounds produced by a variety of microorganisms, such as bacteria and algae. While polyhydroxyalkanoates have been of general interest because of their biodegradable nature, their actual use as a plastic material has been hampered by their thermal instability. For example, poly- 3-hydroxybutyrate (PHB) is a natural energy-storage product of bacteria and algae, and is present in discrete granules within the cell cytoplasm. However, unlike other biologically synthesized polymers such as proteins and polysaccharides, PHB is thermoplastic having a high degree of crystallinity and a well-defined melt temperature of about 180° C. Unfortunately, PHB becomes unstable and degrades at elevated temperatures near its melt temperature. Due to this thermal instability, commercial applications of PHB have been extremely limited.

As a result, investigators have studied other polyhydroxyalkanoates such as poly(3-hydroxybutyrate-co-3-hydroxyvalerate) (PHBV), in the hopes of discovering a polyhydroxyalkanoate having sufficient thermal stability and other suitable chemical and physical properties for use in practical applications. Unfortunately, polyhydroxyalkanoates such as PHB and PHBV are difficult to process into films suitable for backsheet applications. As previously discussed, the thermal instability of PHB makes such processing nearly impossible. Furthermore, the slow crystallization rates and flow properties of PHB and PHBV make film processing difficult. Examples of PHB homopolymer and PHBV copolymers are described in U.S. Pat. No. 4,393,167, Holmes et al., issued Jul. 12, 1983, and U.S. Pat. No. 4,880,592, issued Nov. 14, 1989. PHBV copolymers are commercially available from Imperial Chemical Industries under the tradename BIOPOL. PHBV copolymers are currently produced with valerate contents ranging from about 5 to about 24 mol %. Increasing valerate content decreases the melt temperature, crystallinity, and stiffness of the polymer. An overview of BIOPOL technology is provided in BUSINESS 2000+ (Winter, 1990).

Due to the slow crystallization rate, a film made from PHBV will stick to itself even after cooling; a substantial fraction of the PHBV remains amorphous and tacky for long periods of time. In cast film operations, where the film is immediately cooled on chill rolls after leaving the film die, molten PHBV often sticks to the rolls restricting the speed at which the film can be processed, or even preventing the film from being collected. In blown films, residual tack of the PHBV causes the tubular film to stick to itself after it has been cooled and collapsed for winding.

U.S. Pat. No. 4,880,592, Martini et al., issued Nov. 14, 1989, discloses a means of achieving a PHBV monolayer film for diaper backsheet applications by coextruding the PHBV between two layers of sacrificial polymer, for example a polyolefin, stretching and orienting the multilayer film, and then stripping away the polyolefin layers after the PHBV has had time to crystallize. The remaining PHBV film is then laminated to either water soluble films or water insoluble films such as polyvinylidene chloride or other polyolefins. Unfortunately, such drastic and cumbersome processing measures are necessary in an attempt to avoid the inherent difficulties associated with processing PHBV into films.

Based on the foregoing, there is a need for plastic articles that can biodegrade. In effect such biodegradable articles would facilitate the "recycling" of plastic articles into another usable product, topsoil, through composting. To satisfy this need, there is a preliminary need for a biodegradable polymer which is capable of being easily processed into a plastic article for use in a disposable product.

Objects of the Invention

It is an object of the present invention to provide a biodegradable polyhydroxyalkanoate copolymer.

It is also an object of the present invention to provide plastic articles comprising a biodegradable polyhydroxyalkanoate.

It is also an object of the present invention to provide a method of using a biodegradable polyhydroxyalkanoate to make plastic articles.

It is also an object of the present invention to provide a disposable sanitary garment comprising a film comprising a biodegradable polyhydroxyalkanoate.

SUMMARY

The present invention relates to novel biodegradable polyhydroxyalkanoate copolymers comprising at least two randomly repeating monomer units.

The present invention further relates to plastic articles comprising a biodegradable copolymer, wherein the copolymer comprises at least two randomly repeating monomer units wherein the first monomer unit has the structure

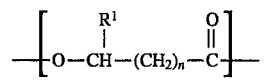

wherein $R^1$ is H, or $C_1$ or $C_2$ alkyl, and n is 1 or 2; the second monomer unit has the structure

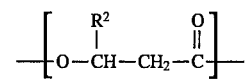

wherein R2 is a $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{19}$ alkyl or alkenyl; and wherein at least 50% of the random repeating monomer units have the structure of the first monomer unit. Such plastic articles include films, sheets, fibers, foams, molded articles, nonwoven fabrics, elastomers, and adhesives.

The present invention further relates to an absorbent article comprising a liquid pervious topsheet, a biodegradable liquid impervious backsheet comprising a film comprising a biodegradable PHA, and an absorbent core positioned between the topsheet and the backsheet.

DETAILED DESCRIPTION

The present invention answers the need for a biodegradable copolymer which is capable of being easily processed into a plastic article. The present invention further answers the need for disposable plastic articles with increased biodegradability and/or compostability.

As used herein, "ASTM" means American Society for Testing and Materials.

As used herein, "comprising" means that other steps and other ingredients which do not affect the end result can be added. This term encompasses the terms "consisting of" and "consisting essentially of".

As used herein, "alkyl" means a saturated carbon-containing chain which may be straight or branched; and substituted (mono- or poly-) or unsubstituted.

As used herein, "alkenyl" means a carbon-containing chain which may be monounsaturated (i.e., one double bond in the chain) or polyunsaturated (i.e., two or more double bonds in the chain); straight or branched; and substituted (mono- or poly-) or unsubstituted.

As used herein, "PHA" means a polyhydroxyalkanoate of the present invention.

As used herein, "PHB" means the homopolymer poly-(3-hydroxybutyrate).

As used herein, "PHBV" means the copolymer poly(3-hydroxybutyrate-co- 3-hydroxyvalerate ).

As used herein, "biodegradable" means the ability of a compound to ultimately be degraded completely into $CO_2$ and water or biomass by microorganisms and/or natural environmental factors.

As used herein, "compostable" means a material that meets the following three requirements: (1) the material is capable of being processed in a composting facility for solid waste; (2) if so processed, the material will end up in the final compost; and (3) if the compost is used in the soil, the material will ultimately biodegrade in the soil.

For example, a polymer film material present in solid waste submitted to a composting facility for processing does not necessarily end up in the final compost. Certain composting facilities subject the solid waste stream to air classification prior to further processing, in order to separate paper and other materials. A polymer film would most probably be separated from the solid waste stream in such an air classification and therefore not be processed in the composting facility. Nevertheless, it may still be a "compostable" material according to the above definition because it is "capable" of being processed in a composting facility.

The requirement that the material ends up in the final compost typically means that it undergoes a form of degradation in the composting process. Typically, the solid waste stream will be subjected to a shredding step in an early phase of the composting process. As a result, the polymer film will be present as shreds rather than a sheet. In the final phase of the composting process, the finished compost will be subjected to a screening step. Typically, the polymer shreds will not pass through the screens if they have retained the size they had immediately after the shredding step. The compostable materials of the present invention will have lost enough of their integrity during the composting process to allow partially degraded shreds to pass through the screens. However, it is conceivable that a composting facility might subject the solid waste stream to a very rigorous shredding and a rather coarse screening, in which case nondegradable polymers like polyethylene would meet requirement (2). Therefore, meeting requirement (2) is not enough for a material to be compostable within the present definition.

What distinguishes the compostable material as defined herein from material like polyethylene is requirement (3), that the material ultimately biodegrade in the soil. This biodegradability requirement is not essential to the composting process or the use of composting soil. Solid waste and the compost resulting therefrom may contain all kinds of nonbiodegradable materials, for example, sand. However, to avoid a build up of man-made materials in the soil, it is required herein that such materials be fully biodegradable. By the same token, it is not at all necessary that this biodegradation be fast. As long as the material itself and intermediate decomposition products are not toxic or otherwise harmful to the soil or crops, it is fully acceptable that their biodegradation takes several months or even years, since this requirement is present only to avoid an accumulation of man-made materials in the soil.

All copolymer composition ratios recited herein refer to mole ratios, unless specifically indicated otherwise.

The present invention relates to biodegradable copolymers which are surprisingly easy to process into plastic articles, particularly into films as compared to the homopolymer PHB and copolymer PHBV.

As used herein, "plastic article" means a copolymer processed into a film, sheet, fiber, foam, molded article, nonwoven fabric, elastomer or adhesive.

PHAs useful for processing into plastic articles of the present invention comprise at least two randomly repeating monomer units (RRMU). The first RRMU has the structure

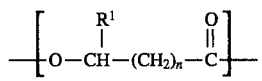

wherein $R^1$ is H, or $C_1$ or $C_2$ alkyl, and n is 1 or 2. The second RRMU has the structure

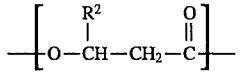

wherein $R^2$ is a $C_4, C_5, C_6, C_7, C_8, C_9, C_{10}, C_{11}, C_{12}, C_{13}, C_{14}, C_{15}, C_{16}, C_{17}, C_{18}$, or $C_{19}$ alkyl or alkenyl.

In one embodiment of the present invention, at least about 50%, but less than 100%, of the RRMUs have the structure of the first RRMU; more preferably at least about 60%; more preferably at least about 70%; more preferably at least about 80%; more preferably still at least about 90%.

When a PHA of the present invention is processed into a film, sheet, or soft elastic fiber, preferably from about 50% to about 99.9% of the RRMUs have the structure of the first RRMU unit; more preferably from about 80% to about 99.5%; more preferably still from about 90% to about 99%.

When a PHA of the present invention is processed into a normal fiber or molded article (e.g., injected or blown molded) preferably from about 80% to about 99.5% of the first RRMUs have the structure of the first RRMU; more preferably from about 90% to about 99.5%; more preferably still from about 95% to about 99.5%.

When a PHA of the present invention is processed into an elastomer or an adhesive, preferably about 50% of the RRMUs have the structure of the first RRMU.

When a PHA of the present invention is processed into a nonwoven, preferably from about 85% to about 99.5% of the RRMUs have the structure of the first RRMU; more preferably from about 90% to about 99.5%; more preferably still from about 95% to about 99.5%.

In one embodiment of the present invention, $R^1$ is a $C_1$ alkyl and n is 1, thereby forming the monomeric repeat unit 3-hydroxybutyrate.

In another embodiment of the present invention, $R^1$ is a $C_2$ alkyl and n is 1, thereby forming the monomeric repeat unit 3-hydroxyvalerate.

In another embodiment of the present invention, $R^1$ is H and n is 2, thereby forming the monomeric repeat unit 4-hydroxybutyrate.

In another embodiment of the present invention, $R^1$ is H and n is 1, thereby forming the monomeric repeat unit 3-hydroxypropionate.

In another embodiment, the copolymer useful in the present invention comprises one or more additional RRMUs having the structure

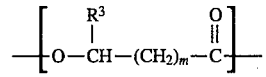

wherein $R^3$ is H, or a $C_1, C_2, C_3, C_4, C_5, C_6, C_7, C_8, C_9, C_{10}, C_{11}, C_{12}, C_{13}, C_{14}, C_{15}, C_{16}, C_{17}, C_{18}$, or $C_{19}$ alkyl or alkenyl; and m is 1 or 2; and wherein the additional RRMUs are not the same as the first RRMU or the second RRMU. Preferably the copolymer comprises 3, 4, 5, 6, 7, 8, 9, 10, 11, 12, 13, 1.4, 15, 16, 17, 18, 19, 20 or more different RRMUs.

In a preferred embodiment of the present invention, $R^3$ is a $C_1, C_2, C_3, C_4, C_5, C_6, C_7, C_8, C_9, C_{10}, C_{11}, C_{12}, C_{13}, C_{14}, C_{15}, C_{16}, C_{17}, C_{18}$, or $C_{19}$ alkyl or alkenyl; and m is 1.

In a preferred embodiment of the present invention, $R^3$ is a $C_1$ alkyl and m is 1, thereby forming the monomeric repeat unit 3-hydroxybutyrate.

In another embodiment of the present invention, $R^3$ is a $C_2$ alkyl and m is 1, thereby forming the monomeric repeat unit 3-hydroxyvalerate.

In another embodiment of the present invention, I:$\{^3$ is H and m is 2, thereby forming the monomeric repeat unit 4-hydroxybutyrate.

In another embodiment of the present invention, $R^3$ is H and m is 1, thereby forming the monomeric repeat unit 3-hydroxypropionate.

Preferably, novel biodegradable PHAs of the present invention comprising two RRMUs have a first RRMU having the structure

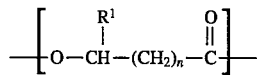

wherein $R^1$ is H, or $C_1$ or $C_2$ alkyl and n is 1 or 2; and a second RRMU having the structure

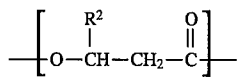

wherein when $R^1$ is $C_1$ or $C_2$ and n is 1, $R^2$ is a $C_{12}$, $C_{13}$, $C_{14}$, $C_{15}$, $C_{16}$, $C_{17}$, $C_{18}$, or $C_{19}$ alkyl or alkenyl; when $R^1$ is $C_1$ or $C_2$ and n is 2, $R^2$ is a $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{19}$ alkyl or alkenyl; and when $R^1$ is H and n is 1 or 2, $R^2$ a $C_4$, $C_5$, $C_6$, $C_7$, $C_8$, $C_9$, $C_{10}$, $C_{11}$, $C_{12}$, $C_{13}$, $C_{14}$, $C_{15}$ $C_{16}$, $C_{17}$, $C_{18}$, or $C_{19}$ alkyl or alkenyl; and wherein at least 50% of the RRMUs have the structure of the first RRMU. Preferably $R^2$ is an alkyl.

Preferably, novel biodegradable PHAs of the present invention comprising three RRMUs, have a first RRMU having the structure

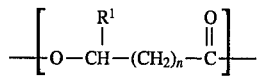

wherein $R^1$ is H, or $C_1$ or $C_2$ alkyl or alkenyl, and n is 1 or 2; a second RRMU having the structure

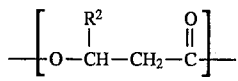

wherein $R^2$ is a $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{19}$ alkyl or alkenyl; and a third RRMU having the structure

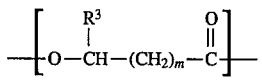

wherein $R^3$ is H, or a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, or $C_{19}$ alkyl or alkenyl; and m is 1 or 2; wherein at least 50% of the RRMUs have the structure of the first RRMU; and wherein the third RRMUs is not the same as the first randomly repeating monomer unit or the second randomly repeating monomer unit.

Synthesis of Biodegradable PHAs

The biodegradable PHAs of the present invention can be synthesized by synthetic chemical or biological based methods. A chemical approach involves the ring-opening polymerization of 13-lactone monomers as described below. The catalysts or initiators used can be 8 variety of materials such as aluminoxsnes, distannoxanes, or alkoxy-zinc and alkoxy-aluminum compounds (see Agostini, D. E., J. B. Lando, and J. R. Shelton, J. POLYM. SCI. PART A-1, Vol. 9, pp. 2775–2787 (1971); Gross, R. A., Y. Zhang, G. Konrad, and R. W. Lenz, MACROMOLECULES, Vol. 21, pp. 2657–2668 (1988); and Dubois, P., I. Barakat, R. Jérôme, and P. Teyssié, MACROMOLECULES, Vol. 26, pp. 4407–4412 (1993); Le Borgne, A. and N. Spassky, POLYMER, Vol. 30. pp. 2312–2319 (1989); Tanahashi, N., and Y. Doi, MACROMOLECULES, Vol. 24, pp. 5732–5733 (1991); Hori, Y., M. Suzuki, Y. Takahashi. A. Ymaguchi, and T. Nishishita, MACROMOLECULES, Vol. 26, pp. 4388–4390 (1993); and Kemnitzer. J. E., S. P. McCarthy, and R. A. Gross, MACROMOLECULES, Vol. 26, pp. 1221–1229 (1993)). The production of isotactic polymer can be accomplished by polymerization of an enantiomerically pure monomer and a non-racemizing initiator, with either retention or inversion of configuration of the stereocenter, or by polymerization of racemic monomer with an initiator which preferentially polymerizes one enantiomer. For example:

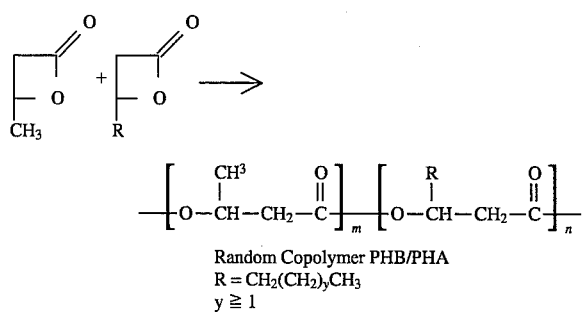

Random Copolymer PHB/PHA
$R = CH_2(CH_2)_yCH_3$
$y \geq 1$

The naturally derived PHAs of the present invention are isotactic and have the R absolute configuration at the stereocenters in the polymer backbone. Alternatively, isotactic polymers may be made where the configuration of the stereocenters is predominantly S. Both isotactic materials will have the same physical properties and most of the same chemical reactivities except when a stereospecific reagent, such as an enzyme, is involved. Atactic polymers, polymers with random incorporation of R and S stereocenters, can be produced from racemic monomers and polymerization initiators or catalysts that show no preference for either enantiomer while such initiators or catalysts often polymerize monomers of high optical purity to isotactic polymer (e.g., distannoxane catalysts) (see Hori, Y., M. Suzuki, Y. Takahashi, A. Yamaguchi. T. Nishishita, MACROMOLECULES, Vol. 26, pp. 5533–5534 (1993)). Alternatively, isotactic polymer can be produced from racemic monomers if the polymerization catalyst has an enhanced reactivity for one enantiomer over the other. Depending on the degree of preference, separate R or S.. stereohomopolymers, stereo-block copolymers, or a mixture of stereo-block copolymers and stereo-homopolymers may be produced (see Le Borgne, A. and N. Spassky, N., POLYMER, Vol. 30, pp. 2312–2319 (1989); Tanahashi, N., and Y. Doi, MACROMOLECULES, Vol. 24, pp. 5732–5733 (1991); and Benvenuti, M. and R. W. Lenz, J. POLYM. ScI.: PART A: POLYM. CHEM., Vol. 29, pp. 793–805 (1991)). Some initiators or catalysts are known to produce predominantly syndiotactic polymers, polymers with alternating R and S stereocenter repeat units, from racetalc monomers (see Kemnitzer, J. E., S. P. McCarthy and R. A. Gross, MACROMOLECULES, Vol. 26, pp. 1221–1229 (1993)) while some initiators or catalysts may produce all three types of stereopolymers (see Hocking, P. J. and R. H. Marchessault, POLYM. BULL., Vol. 30, pp. 163–170 (1993)).

For example, preparation of poly(3-hydroxybutyrate-co-3hydroxyalkanoate) copolymers wherein the 3-hydroxyalkanoate comonomer is a 3-alkyl-β-propiolactone wherein the alkyl group is at least 3 carbons long, are carried out in the following manner. Proper precautions are made to exclude air and moisture. The lactone monomers (purified, dried, and stored under inert atmosphere), β-butyrolactone and a 3-alkyl-β-propiolactone in the desired molar ratio, are charged via syringe or canula to an oven-dried, argon-purged, and flamed borosilicate-glass tube or flask capped with a rubber septum. The polymerization catalyst is added as a toluene solution via syringe. The tube is carefully swirled to mix the reagents (but not contact the rubber septum) and then heated in an oil bath at the desired temperature for the prescribed time. As the reaction proceeds the mixture becomes viscous and may solidify. If isotactic polymer is produced, solid polymer precipitates out until the entire mass solidifies. The product can then be cooled, removed from the tube, and rid of residual monomer by vacuum drying. Alternatively, the product can be dissolved in an appropriate solvent (e.g., chloroform) and recovered by precipitation in a nonsolvent (e.g., ether-hexane mixture, 3:1 v/v), and vacuum dried. Molecular weight is determined by standard methods such as size exclusion chromatography (SEC, also known as gel permeation chromatography or GPC). The comonomer content of the polymers is determined by nuclear magnetic resonance (NMR).

In a preferred method of synthesizing the PHAs of the present invention, the initiator is an alkylzinc alkoxide, as disclosed in the U.S. patent application entitled "Polymerization of Beta-Substituted-Beta-Propiolactones Initiated by Alkylzinc Alkoxides", L. A. Schechtman and J. J. Kemper, assigned to The Procter and Gamble Company, filed Jan. 28, 1994. Such initiators have the general formula $R^1ZnOR^2$, wherein $R^1$ and $R^2$ are independently a $C_1-C_{10}$ alkyl. In a preferred method of synthesis, the initiator is selected from the group consisting of ethylzinc isopropoxide, methylzinc isopropoxide, ethylzinc ethoxide, or ethylzinc methoxide; more preferably ethylzinc isopropoxide.

Other Copolymers useful in the present invention can be made by substituting the starting materials (monomers) in the above procedure with 3-alkyl-13-lactones corresponding to the monomer units desired in the final copolymer product.

Alternatively, biological synthesis of the biodegradable PHAs useful in the present invention may be carried out by fermentation with the proper organism (natural or genetically engineered) with the proper feedstock (single or multicomponent). Biological synthesis may also be carried out with botanical species genetically engineered to express the Copolymers of interest (see World Patent Application No. 93-02187, Somerville, Poirier and Dennis, published Feb. 4, 1993; and U.S. patent application Ser. No. 08/108, 193, Somerville, Nawrath and Poirier, filed Aug. 17, 1993; and Poole, R., SCIENCE, Vol. 245, pp. 1187–1189 (1989)).

Crystallinity

The volume percent crystallinity ($\Phi_c$) of a semi-crystalline polymer (or copolymer) often determines what type of end-use properties the polymer possesses. For example, highly (greater than 50%) crystalline polyethylene polymers are strong and stiff, and suitable for products such as plastic milk containers. Low crystalline polyethylene, on the other hand, is flexible and tough, and is suitable for products such as food wraps and garbage bags. Crystallinity can be determined in a number of ways, including x-ray diffraction, differential scanning calorimetry (DSC), density measurements, and infrared absorption. The most suitable method depends upon the material being tested.

X-ray diffraction is most appropriate when little is known about the thermal properties of the material and crystal structural changes may occur. The basic principle relies on the fact that amorphous parts of the material scatter x-rays in a diffuse or broad range of angles, while crystals diffract x-rays into sharp, precisely defined angles. The total scattered intensity is constant, however. This allows calculation of the amount of crystalline material in a sample if the amorphous and crystalline diffracted intensities can be separated. A very precise method has been developed by Ruland, which can detect differences in percent crystallinity as small as 2% (see Vonk, C., F. J. Balta-Calleja, X-RAY SCATTERING FROM SYNTHETIC POLYMERS, Elsevier: Amsterdam, (1989); and Alexander, L., X-RAY DIFFRACTION METHODS IN POLYMER SCIENCE, Robert Kreiger Pub. Co., New York, (1979)).

Upon melting, crystals require a fixed amount of heat at the melting temperature transforming from crystalline to molten matter. This heat of fusion can be measured by a number of thermal techniques, the most popular being DSC. If the heat of fusion of a 100% crystalline material is known, and no significant annealing, or melt/recrystallization phenomena occur upon heating to the melt, then DSC can quite accurately determine weight fraction crystallinity (see THERMAL CHARACTERIZATION OF POLYMER MATERIALS, E. Turi, Ed., Academic Press, New York, (1980); and Wunderlich, B., MACROMOLECULAR PHYSICS, Academic Press, New York, (1980)).

If the densities of the pure crystalline and pure amorphous material is known then density measurements of a material can yield the degree of crystallinity. This assumes additivity of specific volumes, but this requirement is fulfilled for polymers (or copolymers) of homogeneous structure. This method depends on careful sample preparation so that no bubbles or large voids exist in the sample.

If purely crystalline and amorphous absorption bands can be identified, then the infrared absorption spectrum offers a convenient way of determining crystallinity. (see Tadokoro, H., STRUCTURE OF CRYSTALLINE POLYMERS, John Wiley & Sons, New York, (1979)).

It should be noted that different techniques will often give rise to slightly different values of $\Phi_c$, because they are based on different physical principles. For example, density measurements often give higher values than x-ray diffraction. This is due to the continuous changing of the density in the interface between crystalline and amorphous polymer (or copolymer) material. While x-ray diffraction does not detect this matter as crystalline, density measurements will be affected by this interface region.

In general, PHAs of the present invention preferably have a crystallinity of from about 0.1% to about 99% as measured via x-ray diffraction; more preferably from about 2% to about 80%; more preferably still from about 20% to about 70%.

When a PHA of the present invention is to be processed into a film, the amount of crystallinity in such PHA is more preferably from about 2% to about 65% as measured via x-ray diffraction; more preferably from about 5% to about 50%; more preferably still from about 20% to about 40%.

When a PHA of the present invention is to be processed into a sheet, the amount of crystallinity in such PHA is more preferably from about 0.1% to about 50% as measured via x-ray diffraction; more preferably from about 5% to about 50%; more preferably still from about 20% to about 40%.

When a PHA of the present invention is to be processed into a normal fiber or a nonwoven fabric, the amount of crystallinity in such PHA is more preferably from about 60% to about 99% as measured via x-ray diffraction; more preferably from about 70% to about 99%; more preferably still from about 80% to about 99%.

When a PHA of the present invention is to be processed into a soft elastic fiber, the amount of crystallinity in such PHA is more preferably from about 30% to about 80% as measured via x-ray diffraction; more preferably from about 40% to about 80%; more preferably still from about 50% to about 80%.

When a PHA of the present invention is to be processed into a molded article, the amount of crystallinity in such PHA is more preferably from about 10% to about 80% as measured via x-ray diffraction; more preferably from about 20% to about 70%; more preferably still from about 30% to about 60%.

When a PHA of the present invention is to be processed into an elastomer or adhesive, the amount of crystallinity in such PHA is more preferably less than about 50% as measured via x-ray diffraction; more preferably less than about 30%; more preferably still less than about 20%.

Melt Temperature

Preferably, the biodegradable PHAs of the present invention have a melt temperature (Tm) of from about 30° C. to about 160° C., more preferably from about 60° C. to about 140° C., more preferably still from about 90° C. to about 120° C.

Plastic Articles Comprising PHA

The PHAs of the present invention can be processed into a variety of plastic articles, including but not limited to, films, sheets, fibers, foams, molded articles, nonwoven fabrics, elastomers, and adhesives.

A. Films

In one embodiment of the present invention, the plastic article is a film. As used herein, "film" means an extremely thin continuous piece of a substance having a high length to thickness ratio and a high width to thickness ratio. While there is no requirement for a precise upper limit of thickness, a preferred upper limit would be 0.254 mm, more preferably still about 0.01 mm, more preferably still about 0.005 mm. The protective value of any film depends on its being continuous, i.e., without holes or cracks, since it must be an efficient barrier to molecules such as atmospheric water vapor and oxygen. The film of the present invention can be employed in a variety of disposable products including, but not limited to, disposable diapers, shrink-wrapping (e.g., food wraps, consumer product wraps, pallet and/or crate wraps, and the like), or bags (grocery bags, food storage bags, sandwich bags, resealable "Ziploc®"-type bags, garbage bags, and the like). In a preferred embodiment of the present invention, the film of the present invention is liquid impervious and suitable for use in absorbent disposable sanitary garments such as disposable diapers, feminine hygiene products and the like. More preferably, films of the present invention, in addition to increased biodegradability and/or compostability, have the following properties:

a) a machine direction (MD) tensile modulus from about 10,000 to about 100,000 lbs./sq. in. ($6.895 \times 10^8$ dynes/sq. cm to $6.895 \times 10^9$ dynes/sq. cm), b) a MD tear strength of at least 70 grams per 25.4 µm of thickness, c) a cross machine direction (CD) tear strength of at least 70 grams per 25.4µ of thickness, d) an impact strength of at least 12 cm as measured by falling ball drop, e) a moisture transport rate less than about 0.0012 grams per square centimeter per 16 hours, f) a modulus at 60° C. of at least $5.52 \times 10^7$ dynes/sq. cm (800 lbs./sq. in), and g) a thickness from about 12 µm to about 75 µm.

Methods for testing for such performance criteria are discussed in more detail below.

Prior to Applicants' invention, polyhydroxyalkanoates studied for use in commercial plastics production presented significant impediments to their use in plastics. As discussed above, polyhydroxyalkanoates such as PHB and the copolymer PHBV are difficult to process due to their thermal instability. Furthermore, such polyhydroxyalkanoates were especially difficult to process into films due to their slow crystallization rate. Applicants have found that PHA copolymers of the present invention, which comprise a second RRMU as defined above having an alkyl branch of at least three (3) carbons, are surprisingly easier to process into films, especially as compared to PHB or PHBV. Applicants surprisingly discovered, such linear, random copolymers with a limited number of medium sized (e.g., $C_3$– $C_{19}$) branches provide, in addition to biodegradability, the following properties, particularly as compared to PHB or PHBV: a) a lower melt temperature, b) a lower degree of crystallinity, and c) an improved melt rheology.

Without being bound by theory, Applicants believe characteristics a) and b) are achieved by exclusion of the second RRMU from the crystal lattice of the first RRMU, thereby resulting in a decreased temperature for thermal processing and improved stiffness and elongation properties. Again, without being bound by theory, Applicants believe characteristic c) is achieved by increased entanglement between the copolymer chains due to the side chains of the second RRMU. Such increased entanglement may occur by increased hydrodynamic volume of the copolymer (e.g., the second monomer unit creates kinks in the helical structure), the "hooking" or "catching" of the side chains on different copolymer backbones while in the melt, or the decreased chain scission due to the lower Tm (i.e., the enlarged thermal process window).

1. Performance Criteria and Test Methods for Films

For a film to perform Satisfactorily as a compostable disposable diaper backsheet, it must be made of resins or structures that are biodegradable and it must demonstrate the following properties of high strength, adequate fluid barrier, appropriate modulus or flexibility, and adequately high melting point.

The backsheets of disposable diapers must have sufficient strength both to process on a high speed disposable diaper converting machine and to provide a "wetproof" barrier in use on an infant. It must be sufficiently wetproof so that the clothing or bedding, either that of the infant or of the caregiver, is not wet or soiled. It must have a modulus or flexibility that is, at the same time, low enough to be a soft, pleasing material to be used as the outer covering of an infant diaper yet high enough to handle easily on high speed disposable diaper converters without wrinkling, folding, or creasing. It must have sufficient resistance to heat such that it will not deform, melt, or permanently loose strength in typical hot storage conditions or loose its integrity on high speed disposable diaper converters which typically use hot melt adhesives to bond the components of a disposable diaper together.

Films that are sufficiently strong to be suitable as biodegradable and/or compostable backsheets for disposable diapers preferably demonstrate two properties: (a) resistance to rupture from a dropped weight and (b) resistance to tearing in both the machine direction of manufacture and the cross-machine direction of manufacture. Preferred backsheets of the present invention can withstand the drop of a spherical steel ball of about 19 millimeters in diameter and 27.6 to 28.6 gram mass from a height of 12 centimeters so that at least 50% of the tests result in no rupture of any size (deformation is acceptable). Preferred materials are those that exhibit 50% or less failures from a height of more than 20 centimeters. Similarly, acceptable backsheets of the present invention demonstrate an average tear propagation resistance of 70 grams per 25.4 micron thickness of material in both the machine direction and crossmachine direction of manufacture when a standard Elmendoff pendulum-type test device, such as Elmendorf Model No. 60-100, is employed against 16 plies of material which have been prepared with a cut or notch according to TAPPI Method T 414om-88. More preferable are those backsheets that demonstrate tear propagation resistances of 200 or more grams per 25.4 micron thickness in the cross-machine direction because these are particularly good at avoiding a tendency to fail in use by splitting.

It has also been found that films of sufficient barrier to moisture transport are those that permit less than 0.0012 grams of synthetic urine to pass into an absorbent paper towel per square centimeter of area per 25.4 micron thickness for every 16 hours of time when the test film is located between the absorbent paper towel and a typical absorbent gelling material-containing diaper core and a pressure simulating that of a baby. The specific conditions of the test are that the area of the core is larger than that of the test material, the core is loaded with synthetic urine to its theoretical capacity and it is under a weight of about 35 g/cm$^2$ (0.5 psi).

It has also been found that materials of sufficient heat resistance demonstrate a Vicat softening point of at least 45° C. Vicat softening is tested using a Heat Distortion Apparatus Model No. CS-107 or equivalent and a modification of ASTM D-1525. The modification is in the preparation of the sample. A 19 square millimeter size film of 4.5 to 6.5 mm thickness is prepared for Vicat needle penetration tests by melting the material to be tested into a mold using a temperature of 120° C. and pressure of 7.031× 10$^5$ g/cm$^2$ (10,000 psi) (using a Carver or similar press) for two minutes after a warm-up period of at least 2 minutes. The Vicat softening point is the temperature at which a flat-ended needle of 1 sq. mm circular cross section will penetrate the sample to a depth of 0.1 cm under a load 1000 g using a uniform temperature rise rate of 50° C. per hour.

It has also been found that materials of sufficient machine direction modulus demonstrate a 1% secant-type modulus above at least about 6.895× 10$^8$ dynes/cm$^2$ (10,000 psi) and below about 6.895×10$^9$ dynes/cm$^2$ (100,000 psi). The test is performed on an electronic tensile test machine such as the Instron Model 4201. A 2.54 cm wide strip of material, preferably of 0.00254 cm in thickness, is cut to a length of about 30 cm with the longer dimension parallel to the machine direction of the material. The test strip is clamped into the jaws of the tensile testor so that the gauge or actual length of the material tested is 25.4 cm The jaws are separated at a slow speed in the range of 2.54 cm per minute to 25.4 cm per minute and a stress-strain curve is plotted on a chart within an attached recording device. The 1% secant modulus is determined by reading the stress or tensile from the chart at the 1% elongation strain point. For example, the 1% strain point is achieved when the distance between jaws has increased by 0.254 cm. When the jaws are separating at the rate of 2.54 cm per minute and the recording device is running at a speed of 25.4 cm per minute, the 1% strain point will be located at a distance of 2.54 cm from the initial point. The tensile response is divided by the thickness of the sample material if it is not 0.00254 cm in thickness. Particularly soft, and therefore preferred, materials exhibit 1% secant moduli in the range of 6.895×10$^8$ to 2.068× 10$^9$ dynes/cm$^2$ (10,000 to 30,000 psi).

Since absorbent articles may experience temperatures as high as 140° F. (60° C.) during warehouse storage or shipping in trucks or railcars, it is important that the backsheet film and other components retain their integrity at these temperatures. Although it is expected that the modulus of the films will decrease somewhat between 20° C. and 60° C., the modulus should not decrease too far and allow the film to deform in the package before it reaches the end user.

For example, a polyethylene backsheet with a room temperature modulus of about 4×10$^9$ dynes/cm$^2$ (58,000 psi) may have a 60° C. modulus of 1.2×10$^9$ dynes/cm2 (18,560 psi) which is acceptable. A softer polyethylene backsheet with a room temperature modulus of about 8.0× 10$^8$ dynes/cm$^2$ (11,600 psi) may have a 60° C. modulus of about 3.5×10$^8$ dynes/cm$^2$ (5,076 psi) which is still acceptable. In general, an acceptable backsheet film of the present invention will have a 60° C. modulus of at least 5.52×10$^7$ dynes/cm$^2$ (800 psi).

The modulus dependence on temperature, also called a modulus/temperature spectrum, is best measured on a dynamic mechanical analyzer (DMA) such as a Perkin Elmer 7 Series/Unix TMA 7 Thermomechanical Analyzer equipped with a 7 Series/Unix DMA 7 Temperature/Time software package, hereinafter referred to as the DMA 7, available from the Perkin-Elmer Corporation of Norwalk, Connecticut. Many other types of DMA devices exist, and the use of dynamic mechanical analysis to study the modulus/temperature spectra of polymers is well known to those skilled in the an of polymer (or copolymer) characterization. This information is well summarized in two books, the first being DYNAMIC MECHANICAL ANALYSIS OF POLYMERIC MATERIAL, MATERIALS SCIENCE MONOGRAPHS VOLUME 1 by T. Murayama (Elsevier Publishing Co., 1978) and the second being MECHANICAL PROPERTIES OF POLYMERS AND COMPOSITES, VOLUME 1 by L. E. Nielsen (Marcel Dekker, 1974).

The mechanism of operation and procedures for using the DMA 7 are found in Perkin-Elmer Users' Manuals 0993–8677 and 0993–8679, both dated May, 1991. To those skilled in the use of the DMA 7, the following run conditions should be sufficient to replicate the 60OC modulus data presented hereinafter.

To measure the modulus/temperature spectrum of a film specimen, the DMA 7 is set to run in temperature scan mode and equipped with an extension measuring system (EMS). A film specimen approximately 3 mm wide, 0.0254 mm thick, and of sufficient length to allow 6 to 8 mm of length between the specimen grips is mounted in the EMS. The apparatus is then enclosed in an environmental chamber swept continuously with helium gas. Stress is applied to the film in the length direction to achieve a deformation or strain of 0.1 percent of the original length. A dynamic sinusoidal strain is applied to the specimen at a frequency of 5 cycles per second. In the temperature scan mode, the temperature is increased at a rate of 3.0° C./minute from 25° C. to the point where the specimen melts or breaks, while the frequency and stress are held constant. Temperature-dependent behavior is characterized by monitoring changes in strain and the phase difference in time between stress and strain. Storage modulus values in Pascals are calculated by the computer along with other data and displayed as functions of temperature on a video display terminal. Normally the data are saved on computer disk and a hard copy of the storage modulus/ temperature spectrum printed for further review. The 60° C. modulus is determined directly from the spectrum.

2. Method of Film Manufacture

The films of the present invention used as backsheets having increased biodegradability and/or compostability may be processed using conventional procedures for producing single or multilayer films on conventional film-making equipment. Pellets of the PHAs of the present invention can be first dry blended and then melt mixed in a film extruder. Alternatively, if insufficient mixing occurs in the film extruder, the pellets can be first dry blended and then melt mixed in a precompounding extruder followed by repelletization prior to film extrusion.

The PHAs of the present invention can be melt processed into films using either cast or blown film extrusion methods both of which are described in PLASTICS EXTRUSION TECHNOLOGY-2nd Ed., by Allan A. Griff (Van Nostrand Reinhold-1976). Cast film is extruded through a linear slot die. Generally the flat web is cooled on a large moving polished metal roll. It quickly cools, and peels off this first roll, passes over one or more auxiliary cooling rolls, then through a set of rubber-coated pull or "haul off" rolls, and finally to a winder. A method of making a cast backsheet film for the absorbent articles of the present invention is described in an example below.

In blown film extrusion, the melt is extruded upward through a thin annular die opening. This process is also referred to as tubular film extrusion. Air is introduced through the center of the die to inflate the tube and thereby causing it to expand. A moving bubble is thus formed which is held at a constant size by control of internal air pressure. The tube of film is cooled by air, blown through one or more chill rings surrounding the tube. The tube is then collapsed by drawing it into a flattening frame through a pair of pull rolls and into a winder. For backsheet applications the flattened tubular film is subsequently slit open, unfolded, and further slit into widths appropriate for use in products.

Both cast film and blown film processes can be used to produce either monolayer or multilayer film structures. For the production of monolayer films from a single thermoplastic material or blend of thermoplastic components only a single extruder and single manifold die are required.

For the production of multilayer films of the present invention, coextrusion processes are preferably employed. Such processes require more than one extruder and either a coextrusion feedblock or multi-manifold die system or combination of the two to achieve the multilayer film structure.

U.S. Pat. Nos. 4,152,387, and 4,197,069, disclose the feedblock principle of coextrusion. Multiple extruders are connected to the feedblock which employs moveable flow dividers to proportionally change the geometry of each individual flow channel in direct relation to the volume of polymer passing through said flow channels. The flow channels are designed such that at their point of confluence, the materials flow together at the same flow rate and pressure eliminating interfacial stress and flow instabilities. Once the materials are joined in the feedblock, they flow into a single manifold die as a composite structure. It is important in such processes that the melt viscosities and melt temperatures of the materials do not differ too greatly; otherwise flow instabilities can result in the die leading to poor control of layer thickness distribution in the multilayer film.

An alternative to feedblock coextrusion is a multi-manifold or vane die as disclosed in aforementioned U.S. Pat. Nos. 4,152,387, 4,197,069, and in U.S. Pat. No. 4,533,308. Whereas in the feedblock system melt streams are brought together outside and prior to entering the die body, in a multi-manifold or vane die each melt stream has its own manifold in the die where the polymers spread independently in their respective manifolds. The melt streams are married near the die exit with each melt stream at full die width. Moveable vanes provide adjustability of the exit of each flow channel in direct proportion to the volume of material flowing through it, allowing the melts to flow together at the same linear flow rate, pressure, and desired width.

Since the melt flow properties and melt temperatures of the processed materials may vary widely, use of a vane die has several advantages. The die lends itself toward thermal isolation characteristics wherein materials of greatly differing melt temperatures, for example up to 175° F. (80° C.), can be processed together.

Each manifold in a vane die can be designed and tailored to a specific polymer (or copolymer). Thus the flow of each polymer is influenced only by the design of its manifold, and not by forces imposed by other polymers. This allows materials with greatly differing melt viscosities to be coextruded into multilayer films. In addition, the vane die also provides the ability to tailor the width of individual manifolds, such that an internal layer, for example a water soluble biodegradable polymer like Vinex 2034, can be completely surrounded by water insoluble materials leaving no exposed edges susceptible to water. The aforementioned patents also disclose the combined use of feedblock systems and vane dies to achieve more complex multilayer structures.

The multilayer films of the present invention may comprise two or more layers. In general, balanced or symmetrical three-layer and five-layer films are preferred. Balanced three-layer multilayer films comprise a center core layer and two identical outer layers, wherein said center core layer is positioned between said two outer layers. Balanced five-layer multilayer films comprise a center core layer, two identical tie layers, and two identical outer layers, wherein said center core layer is positioned between said two tie layers, and a tie layer is positioned between said center core layer and each outer layer. Balanced films, though not essential to the films of the present invention, are less prone to curling or warping than unbalanced multilayer films.

In three layer films, the center core layer may comprise 30 to 80 percent of the films' total thickness and each outer layer comprises 10 to 35 percent of the films' total thickness. Tie layers, when employed, each comprise from about 5 percent to about 10 percent of the films' total thickness.

B. Sheets

In another embodiment of the present invention, the plastic article is a sheet. As used herein, "sheet" means a very thin continuous piece of a substance, having a high length to thickness ratio and a high width to thickness ratio, wherein the material is thicker than 0.254 mm. Sheeting shares many of the same characteristics as film in terms of properties and manufacture, with the exception that sheeting is stiffer, and has a self-supporting nature. Such differences in stiffness and support result in some modification of the manufacturing methods.

1. Methods of Manufacture

Sheets, because of thickness and consequent stiffness, cannot be blown as a film. However many other of the same processes used to make film can be modified to make sheeting. One example is cast extrusion which is described previously. In addition to extrusion, sheeting is also made via rolling and calendering.

a. Rolling

Rolling produces a film with predominately machine direction orientation by accelerating the film from a nip point where the thickness is reduced (ENCYCLOPEDIA OF POLYMER SCIENCE AND ENGINEERING, Vol. 8, pp. 88–106, John Wiley and Sons, New York, (1986); hereinafter referred to as "EPSE-I"). Large forces are found at the nip point, but overall orientation can be increased over other forms of machine direction orientation.

b. Calendering

To produce an unoriented cast film or sheet with high throughput, calendering is used (G. W. Eghmy, Jr. in MODERN PLASTICS, J. Agrandoff, ed. Encyclopedia, Vol 59(10A), pp. 220–222 (1982) and R. A. Elden and A. D. Swan, CALENDERING OF PLASTICS, American Elsevier Co., Inc., New York, (1971)). The calendering process employs stacks of specially hardened, driven rolls, supported in a manner so they may be bent or skewed in position relative to each other during operation. This is to control thickness in the calendered material. Calenders are usually made up of four rolls that form three nips. These nips are the feed, metering and finishing nips. The feed nip is where the polymer is supplied, mixed, and heated. The metering nip reduces the thickness of the sheet to the approximate final thickness. The finishing nip adjusts the gauge of the sheet by varying the position of the third or middle roll. (see EPSE-2)

C. Fibers

In another embodiment of the present invention, the plastic article is a fiber. As used herein, "fiber" refers to a flexible, macroscopically homogeneous body having a high length-to-width ratio and a small cross section. A general overview of fibers can be found in the ENCYCLOPEDIA OF POLYMER SCIENCE AND ENGINEERING, Vol. 6, p. 647–755 and pp. 802–839, John Wiley and Sons, New York. (1986) (hereinafter referred to as "EPSE- 2"). The fibers of the present invention are useful as textiles in yarns for garments. The fibers of the present invention are also useful for manufacturing lightweight fibrous materials useful in agricultural applications to protect, promote, or control plant growth. They are also used in green house thermal screens, crop row covers, turf covers, weed barriers and hydroponics. Key properties are light, air, and moisture permeability. An important aspect is cost effectiveness when considered in terms of weight, strength, and dimension stability.

An elastomeric fiber is a fiber that consists of polymers (or copolymers) with a main glass transition temperature much below room temperature (see EPSE-2). This criterion excludes some fibers with elastic properties, such as crimped hard fibers, but allows inclusion of multi-constituent fibers where one of the constituents is an elastomer. All elastomeric fibers are characterized by a higher elongation at break, lower modulus, and higher recovery from large deformation than normal fibers.

1. Methods of Fiber Manufacture

The fibers of the present invention may be processed using a variety of conventional techniques well-known in the art including, but not limited to, melt spinning, dry spinning, and wet spinning. Combinations of these three basic processes are often used.

In melt spinning a PHA of the present invention is heated above its melting point and the molten PHA is forced through a spinneret. A spinneret is a die with many small orifices which are varied in number, shape and diameter (see EPSE-2). The jet of molten PHA is passed through a cooling zone where the PHA solidifies and is then transferred to post-drawing and take-up equipment.

In dry spinning, a PHA of the present invention is dissolved and the PHA solution is extruded under pressure through a spinneret (see EPSE-2). The jet of PHA solution is passed through a heating zone where the solvent evaporates and the filament solidifies.

In wet spinning, a PHA of the present invention is also dissolved and the solution is forced through a spinneret which is submerged in a coagulation bath (see ESPE-2). As the PHA solution emerges from the spinneret orifices within the coagulation bath, the PHA is either precipitated or chemically regenerated. Usually, all these processes need further drawing for useful properties to be obtained, for example to serve as textile fibers. "Drawing" refers to stretching and attenuation of fibers to achieve an irreversible extension, induce molecular orientation, and develop a fiber-fine structure (see ESPE-2). This fine structure is characterized by a high degree of crystallinity and by orientation of both the crystallites and the amorphous PHA chain segments.

D. Foams

In another embodiment of the present invention, the plastic article is a flexible foam. As used herein, "foam" refers PHA of the present invention whose apparent density has been substantially decreased by the presence of numerous cells distributed throughout its bulk (see ASTM D 883-62T, American Society for Testing and Materials, Philadelphia, Pa., (1962)). Such two-phase gas/solid systems in which the solid is continuous and composed of a synthetic polymer or rubber include cellular polymers (or copolymers), expanded plastics and foamed plastics (ENCYCLOPEDIA OF CHEMICAL TECHNOLOGY, Vol. 11, John Wiley & Sons, New York (1980), hereinafter referred to as "ECT").

The gas phase is distributed into pockets or voids called cells which are classified into two types, open and closed. Open-celled material are foams whose cells are inter-connected such that gases may pass freely through the cells. Closed-cell materials have cells that are discrete and isolated from each other.

Foams are further categorized into flexible and rigid foams. This classification is based on a particular ASTM test procedure (see ASTM D, Vol. 37, pp. 1566–1578, American Society of Testing and Materials, Philadelphia, Pa., (1978)). A flexible foam is a foam which does not rupture when a 20×2.5×2.5 cm piece is wrapped around a 2.5 cm mandrel at a uniform rate of 1 lap/5s at 15–25° C. Foams that do rupture under this test are referred to as rigid foams.

Foams find many applications as packaging, comfort cushioning, insulation, and structural components. In the some areas of packaging a foamed material having increased biodegradability and/or compostability would offer superior benefits to currently used packaging such as polystyrene, paper and starch foams. In hot food containers, polystyrene offers significantly higher thermal insulation over the only currently degradable alternative, paper wraps. Foamed articles comprising a PHA of the present invention have the thermal insulating properties of polystyrene, yet are biodegradable and/or compostable. These materials are ideal for hot food take-out and cold food packaging.

Foamed polystyrene chips are used as cushioned packing materials for consumer and industrial goods. Many of these chips end up in landfills. Foamed chips comprising a PHA of the present invention perform as well as polystyrene and have increased biodegradability and/or compostability. Unlike other compostable packaging material such as starch, such PHA chips are resistant to many common solvents and liquids including water.

1. Methods of Foam Manufacture

The foams of the present invention may be processed using conventional procedures well-known to those skilled in the art. A predominant method of foam production involves expanding a fluid polymer (or copolymer) phase to a low density cellular phase and then preserving this state (see ECT). Other processes include leaching out materials that have been previously dispersed in the polymer (or copolymer), sintering small particles and dispersing cellular particles in a polymer (or copolymer). Three steps make up the expansion process. These are cell initiation, cell growth and cell stabilization. Many methods are used to create, grow, and stabilize cells.

Expandable formulations rely on increasing the pressure within the initiated cells relative to that of the surroundings. The cells are stabilized by either chemical (e.g. crosslinking, polymerization) or physical means (crystallization, melt-glass transition). Polystyrene is an example of a polymer that is foamed by of this kind of process. A blowing agent such as isomeric pentanes and hexanes or halocarbons (H. R. Lasman, MODERN PLASTICS, Vol. 42(1A), p. 314 (1964)) is mixed with the polymer (or copolymer) either by heating and allowing the blowing agent to penetrate the polymer (U.S. Pat. No. 2,681,321, issued Jun. 15, 1954, F. Stastny and R. Gaeth, assigned to BASF), or by polymerizing the polystyrene in the presence of the blowing agent (U.S. Pat. No. 2,983,692, issued May 9, 1961, G. F. D'Alelio, assigned to Koppers Co.). Fabrication of articles are usually carried out in multiple steps, the first of which uses steam, hot water or hot air to expand the polymer into low density preformed beads. These preformed beads are aged, sometimes in multiple steps for correct cell size, and then packed into molds and fused together by heat and further expansion (S. J. Skinner, S. Baxter, and P. J. Grey, Trans. J. PLAST. INST. Vol. 32, p. 180 (1964)). Stabilization is accomplished by cooling the polymer to temperatures below its glass transition temperature.

Decompression expansion processes create and grow cells by lowering the external pressure during processing. Cellular polyethylene and polypropylene are often made in this manner. A decomposing blowing agent is premixed with the polymer (or copolymer) and fed through an extruder under elevated temperature and pressure such that the blowing agent partially decomposes. When the material exits the extruder, it enters a lower pressure zone. Simultaneous expansion and cooling take place, resulting in a stable cellular structure owing to rapid crystallization of the polymer (R. H. Hansen, SPE J., Vol. 18, p. 77 (1962), W. T. Higgins, M.D. PLAST., Vol. 31(7), p. 99, (1954)).

Dispersion processes produce foams by directing dispersing solid or gas into the polymer (or copolymer) phase and then, when necessary, stabilizing the mixture (ECT). In one such process, frothing, a gas is mechanically dispersed in the polymer or monomer phase, producing a foam of temporary stability. This foam is then chemically stabilized by crosslinking or polymerization. Latex foam rubber is manufactured in this way (see ECT).

E. Molded Articles

In another embodiment of the present invention, the plastic article is a molded article. As used herein, "molded article" means objects that are formed from polymer or copolymer materials (e.g., PHA) which are injected, compressed, or blown by means of a gas into shape defined by a female mold. These objects can be solid objects like toys, or hollow like bottles and containers.

Injection molding of thermoplastics is a multi-step process by which a PHA of the present invention is heated until it is molten, then forced into a closed mold where it is shaped, and finally solidified by cooling. There are a variety of machines that are used in injection molding. Three common types are ram, screw plasticator with injection, and reciprocating screw devices (see ENCYCLOPEDIA OF POLYMER SCIENCE AND ENGINEERING, Vol. 8, pp. 102–138, John Wiley and Sons, New York, (1986); hereinafter referred to as "EPSE-3"). A ram injection molding machine is composed of a cylinder, spreader, and plunger. The plunger forces the melt in the mold. A screw plasticator with a second stage injection consists of a plasticator, directional valve, a cylinder without a spreader, and a ram. After plastication by the screw, the ram forces the melt into the mold. A reciprocating screw injection machine is composed of a barrel and a screw. The screw rotates to melt and mix the material and then moves forward to force the melt into the mold.

Compression molding in thermoplastics consists of charging a quantity of a PHA of the present invention in the lower half of an open die. The top and bottom halves of the die are brought together under pressure, and then molten PHA conforms to the shape of the die. The mold is then cooled to harden the plastic (see EPSE-3).

Blow molding is used for producing bottles and other hollow objects (see EPSE-3). In this process, a tube of molten PHA known as a parison is extruded into a closed, hollow mold. The parison is then expanded by a gas, thrusting the PHA against the walls of a mold. Subsequent cooling hardens the plastic. The mold is then opened and the article removed.

Blow molding has a number of advantages over injection molding. The pressures used are much lower than injection molding. Blow molding can be typically accomplished at pressures of 25–100 psi between the plastic and the mold surface. By comparison, injection molding pressures can reach 10,000 to 20,000 psi (see EPSE-3). In cases where the PHA has a have molecular weights too high for easy flow through molds, blow molding is the technique of choice. High molecular weight polymers (or copolymers) often have better properties than low molecular weight analogs, for example high molecular weight materials have greater resistance to environmental stress cracking. (see EPSE-3). It is possible to make extremely thin walls in products with blow molding. This means less PHA is used, and solidification times are shorter, resulting in lower costs through material conservation and higher throughput. Another important feature of blow molding is that since it uses only a female mold, slight changes in extrusion conditions at the parison nozzle can vary wall thickness (see EPSE-3). This is an advantage with structures whose necessary wall thicknesses cannot be predicted in advance. Evaluation of articles of several thicknesses can be undertaken, and the thinnest, thus lightest and cheapest, article that meets specifications can be used.

F. Nonwovens

In another embodiment of the present invention, the plastic article is a nonwoven. As used herein "nonwoven" means porous, textile like materials, usually in flat sheet form, composed primarily, or entirely, of fibers assembled in webs that are manufactured by processes other than spinning, weaving, or knitting. A general overview of nonwoven fabrics can be found in the ENCYCLOPEDIA OF POLYMER SCIENCE AND ENGINEERING, Second Edition, Vol. 10, pp. 204–226 (referred to hereafter as "EPSE-4"). Other names for these materials are bonded fabrics, formed fabrics, or engineered fabrics. The thickness of the fabric sheets may vary from 25 mm to several centimeters, and the weight from 10 g/m$^2$ to 1 kg/m$^2$. Nonwoven fabrics have a wide range of physical properties depending on the material and process used in forming the web. A fabric may be self-supporting and stiff as paper or drapable as a conventional cloth fabric.

In contrast to conventional textiles, the fundamental structure of all nonwovens is a web of fibers arranged more or less randomly (NONWOVENS IND., Vol. 17, p. 36 (Mar. 1986), NONWOVENS WORLD, Vol. 1, p. 36 (May–June 1986)). Thus, the key element is the single fiber. Tensile, tear, and tactile properties in the nonwoven arise from adhesive or other chemical and physical bonding, fiber-to-fiber friction created by entanglement, and reinforcement by other materials such as foams and films (see EPSE-4).

1. Method of Manufacture of Nonwoven Fabrics

The nonwoven fabrics of the present invention may be made by conventional techniques known in the art. The production of nonwoven fabrics involves: 1) making fibers of various lengths and diameters; 2) creating a web of these fibers; and 3) bonding of fibers within the web by adhesive, or mechanical-frictional forces created by fiber contact or entanglement. In addition to these steps, reinforcing the web by forming a composite with other materials (e.g., yarns, scrims, films, nettings, and unbonded webs) is sometimes preferred. Variations of one or several of these steps allows for the enormous range of nonwoven fiber types. The term "staple fibers" was originally applied to fibers of natural origin long enough to be processed on textile machinery, but excluding endless filaments, eg, silk. In the present context, as applied to PHA of the present invention, "staple fibers" are of relatively uniform length, ca. 1.3–10.2 cm, with a regular crimp i.e., a three-dimensional wavelike shape. Regenerated and other extruded fibers are endless as formed. They are cut during the manufacturing process to a specified length to meet a processing or market need. Extruded fibers are also produced as continuous filaments without crimp. The processes for forming webs from staple fibers are different from those using continuous filaments. The products obtained from staple and filament fiber webs may differ substantially in properties (see EPSE-4).

The mechanical properties of the fibers as defined by their chemical composition, determine the ultimate properties of the fabric. Web structure and bonding maximize inherent fiber characteristics (see EPSE-4). Other materials that may be used in the nonwovens of the present invention in combination with the PHA are wood pulp; regenerated fibers including viscose rayon and cellulose acetate; and synthetic fibers like poly(ethylene terephthalate) (PET), nylon-6, nylon 6,6, polypropylene (PP), and poly(vinyl alcohol). Facings of disposable diapers or sanitary napkins made from PHA nonwoven fabrics of the present invention preferably feel dry even when the absorbent, inner absorbent layer is saturated. Important fiber characteristics that affect performance include length, diameter, density, crimp, cross section shape, spin-finish (lubricant that is added to the surface of extruded fibers to enhance processability), delustering (small amounts of $TiO_2$ pigment added before extrusion to increase whiteness or to reduce sheen) and the draw ratio.

a. Web-making methods

The characteristics of the fiber web determine the physical properties of the final product. These characteristics depend largely on fiber architecture, which is determined by the mode of web formation. Fiber architecture includes the predominant fiber direction, whether oriented or random, fiber shape (straight, hooked, or curled), the extent of interfiber engagement or entanglement, crimp, and compaction (web-density control). Web characteristics are also influenced by fiber diameter, length, web weight, and chemical and mechanical properties of the polymer (see EPSE- 4).

The choice of method for forming the web is determined by fiber length. Initially, the methods for forming webs from staple-length fibers (fibers long enough to be handled by conventional spinning equipment, usually from about 1.2 to about 20 cm long, but not endless) are based on the textile-carding process, whereas web formation from short fibers is based on papermaking technologies. Although these technologies are still in use, other methods have been subsequently developed. For example, webs are formed from long, virtually endless filaments directly from bulk polymer; both web and fibers are produced simultaneously (see EPSE-4). A variety of web-making methods are known, including carding, air-laying, wet-forming, spinbonding, and meltblowing.

The carding process is derived from the ancient manual methods of fiber carding, where natural staple fibers were manipulated by beds of needles. In carding, clumps of staple fibers are separated mechanically into individual fibers and formed into a coherent web by the mechanical action of moving beds of closely spaced needles.

In the air-laying process, the orientation created by carding is effectively improved by capturing fibers on a screen from an airstream (see U.S. Pat. No. 3,338,992, G. A. Kinney, assigned to E.I. du Pont de Nemours & Co., Inc., issued Aug. 29, 1967). The fibers are separated by teeth or needles and introduced into an airstream. Total randomization would exclude any preferential orientation when the fibers are collected on the screen.

Wet-forming processes employ very short fibers. Initially, webs are formed from short fibers by modified papermaking techniques. The fibers are continuously dispersed in a large volume of water and caught on a moving endless wire screen. Once the web is caught on the screen, it is transferred to belts or felts and dried on heated drums (see EPSE-4).

The spunbonded web process involves making fibers and web simultaneously, directly from bulk polymer. The bulk polymer is melted, extruded, and drawn (often by triboelectric forces) to filaments that are randomized and deposited onto belts as a continuous web. The filaments are virtually endless. The spunbond process produces webs of low crimp filaments in the normal diameter range of about 1.7 dtex (1.5 den) or slightly higher. The birefringence and uniformity of diameter of these filaments are similar to standard textile fibers and filaments (see EPSE-4). Each production line is suitable for a specific polymer and a single-bonding system (see U.S. Pat. No. 4,163,305 (Aug. 7, 1979), V. Semjonow and J. Foedrowitz (to Hoechst AG)).

Webs are also made directly from bulk polymers by the meltblown process (see U.S. Pat. No. 3,322,607, S. L. Jung, assigned to E.I. dupont de Nemours & Co., Inc., May 30, 1967). The molten PHA is forced through very fine holes in a special die into a high velocity airstream where the PHA is formed into very fine, although irregular, filaments of indeterminate lengths. The filaments are simultaneously formed into a web where melting and resolidification, and possibly static forces, hold them together (see EPSE-.4). The web consists primarily of filaments with very fine diameters.

b. Web bonding

The bonding of fibers gives the strength to the web and influences other properties. Both adhesive and mechanical means are used. Mechanical bonding employs the engagement of fibers by frictional forces. Bonding can also be achieved by chemical reaction, i.e., formation of covalent bonds between binder and fibers (see EPSE-4).

G. Elastomers

In another embodiment of the present invention, the plastic article is an elastomer. As used herein "elastomer" refers to materials which exhibit both long-range deformability on application of stress and essentially complete recovery on removal. A general discussion on elastomers can be found in the Encyclopedia of Polymer Science and Engineering, Second Edition, Vol. 5, pp. 106–127 (hereafter referred to as "EPSE-5"). Preferably, an elastomer of the present invention, at room temperature, can be stretched repeatedly to at least twice its original length and, after removal of the tensile load, will immediately and forcibly return to approximately its -original length. Elastomers of the present invention are above the glass-transition temperature Tg and amorphous in the unstressed state to exhibit high local segmental mobility necessary for deformation. The chains are flexible and intermolecular (interchain) forces are weak. The elastomers of the present invention possess a sufficient number of chemical or physical cross-links to form a continuous network in order to restrain chain slippage.

Thermoplastic elastomers of the present invention have many of the properties of conventional elastomers such as vulcanized rubbers, but are processed as thermoplastics rather than thermosets. Transition from a fluid melt to a solid is reversible. Thermoplastic elastomers of the present invention are multiphase systems, where at least one phase is soft and rubbery and another hard. With thermoplastic elastomers, the transition from a processible melt to a solid, rubberlike object is rapid and reversible and takes place upon cooling. Preferably, PHAs of the present invention which are processed into an elastomer have sufficiently high branch content to enable them to act as thermoplastic elastomers, with the crystalline areas acting as the hard segment and the amorphous segments acting as the soft segment. Thermoplastic elastomers of the present invention can be processed on conventional plastics equipment, such as injection molders.

Important structural parameters for thermoplastic elastomers are the molecular weight, the nature of the soft and hard segments, and the ratio of soft to hard segments. The ratio of hard to soft segments effects the total modulus of the elastomer, increasing with the proportion of the hard segments.

Elastomers of the present invention comprising a PHA of the present invention can also be used in blend formulations with other polymers (or copolymers), even non-elastomeric PHAs, to increase impact strength and toughness in stiffer materials.

H. Adhesive

In another embodiment of the present invention, the plastic article is an adhesive. As used herein "adhesive" means a material that joins two other materials, called adherends, together. A general discussion on adhesives can be found in the Encyclopedia of Polymer Science and Engineering, Vol. 1, pp. 547–577, (hereafter referred to as "EPSE-6"). In one embodiment of the present invention, the adhesive is applied as a liquid, preferably of a low viscosity. In the liquid form the adhesive wets the adherend surface and flows into the crevices in the adherend surfaces. The liquid form of the adhesive is obtained by heating to the point that flow occurs, dissolving or dispersing the material in a solvent, or starting with liquid monomers or oligomers that polymerize or react after application. The adhesive then undergoes a phase change to a solid either by cooling, solvent evaporation, or reaction, in order for the joint to acquire the necessary strength to resist shearing forces. However, pressure-sensitive adhesives are an exception, since no phase change occurs.

The PHAs of the present invention may be processed into a variety of adhesives, including but not limited to, hot melt, solution, dispersion and pressure sensitive adhesives.

1. Hot-melt Adhesives

As used herein, "hot-melt adhesive" refers to a thermoplastic polymer or copolymer (e.g., a PHA of the present invention) that is heated to obtain a liquid of flowable viscosity, and, after application, cooled to obtain a solid. Generally, the molecular weight of the adhesive is tailored to provide flowability in the melt, but still be strong enough in the solid form to resist shearing forces experienced in the application. Due to their thermoplastic properties, the PHAs of the present invention are particularly useful as hot-melt adhesives. The primary feature of hot-melt adhesives is the ability of the thermoplastic material to flow above a certain temperature, high above the normal use temperature of the bond. Upon cooling, the material hardens, either through passing through the glass transition temperature of one of the components, or the crystallization temperature. This hardening lends physical integrity to the bond. In PHAs, the mode of solidification is crystallization.

2. Solutions and dispersions.

The adhesives of the present invention may be applied either as solutions, in water or an organic solvent, or in the form of aqueous dispersions. In either form, the solvent must be removed after application for the adhesive to attain the required solid form. The solution or dispersion is usually applied to one of the surfaces to be bonded, and the solvent removed before the second surface is joined; often, heating is required to expedite the drying step. With porous substrates, such as paper or wood, final drying can take place after formation of the joint. Solids contents of the solutions vary from 5 to 95%, although values from 20 to 50% are most common.

As used herein, "dispersion" refers to when adhesives are prepared by true emulsion polymerization or dispersed as larger particles in some carrier fluid. In addition to their economic advantage, dispersions containing 40–50% solids offer lower viscosity than solutions, even if the solids are high molecular-weight polymers (EPSE-6). Adhesive dispersions of the present invention may be prepared by high shear in the presence of surfactants to obtain waterborne formulations, procedures which are well known to those skilled in the art.

3. Pressure-sensitive Adhesives.

Another type of adhesive of the present invention is a pressure-sensitive adhesive. Unlike other adhesives, the pressure-sensitive adhesives do not change their physical state from the initial application, to the final breaking of the adhesive bond. They remain permanently deformable, and may alter under even slight application of pressure. They are adhesives that in dry form are permanently tacky at room temperature and that firmly adhere to surfaces upon mere contact. The most common form of pressure-sensitive adhesive is on a backing, usually in tape form. Common masking tape, for example, is manually applied after the user removes the desired length from a roll. Many bandages are held to the skin by pressure-sensitive adhesives.

Disposable Personal Care Products

The present invention further relates to disposable personal care products comprising a PHA of the present invention. For example, compostable absorbent articles comprising a liquid pervious topsheet, a liquid impervious backsheet comprising a film of the present invention (i.e., a film comprising a PHA of the present invention), and an absorbent core positioned between the topsheet and backsheet. Such absorbent articles include infant diapers, adult incontinent briefs and pads, and feminine hygiene pads and liners.

Additional personal cam products comprising a PHA of the present invention include personal cleansing wipes; disposable health care products such as bandages, wound dressings, wound cleansing pads, surgical gowns, surgical covers, surgical pads; other institutional and health care disposables such as gowns, wipes, pads, bedding items such as sheets and pillowcases, foam mattress pads.

A. Absorbent Articles

Films of the present invention used as liquid impervious backsheets in absorbent articles of the present invention, such as disposable diapers, typically have a thickness of from 0.01 mm to about 0.2 ram, preferably from 0.012 mm to about 0.051 min.

In general, the liquid impervious backsheet is combined with a liquid pervious topsheet and an absorbent core positioned between the topsheet and the backsheet. Optionally, elastic members and tape tab fasteners can be included. While the topsheet, the backsheet, the absorbent core and elastic members may be assembled in a variety of well known configurations, a preferred diaper configuration is described generally in U.S. Pat. No. 3,860,003, entitled "Contractible Side Portion for Disposable Diaper" which issued to Kenneth B. Buell on Jan. 14, 1975.

The topsheet is preferably, soft-feeling, and non-irritating to the wearer's skin. Further, the topsheet is liquid pervious, permitting liquids to readily penetrate through its thickness. A suitable topsheet may be manufactured from a wide range of materials such as porous foams, reticulated foams, apertured plastic films, natural fibers (e.g., wood or cotton fibers), synthetic fibers (e.g., polyester or polypropylene fibers) or from a combination of natural and synthetic fibers. Preferably, the topsheet is made of a hydrophobic material to isolate the wearer's skin from liquids in the absorbent core.

A particularly preferred topsheet comprises staple-length fibers having a denier of about 1.5. As used herein, the term "staple-length fibers" refers to those fibers having a length of at least about 16 min.

There are a number of manufacturing techniques which may be used to manufacture the topsheet. For example, the topsheet may be woven, non-woven, spunbonded, carded, or the like. A preferred topsheet is carded, and thermally bonded by means well known to those skilled in the fabrics art. Preferably, the topsheet has a weight from about 18 to about 25 $g/m^2$, a minimum dried tensile strength of at least about 400 g/cm in the machine direction, and a wet tensile strength of at least about 55 g/cm in the cross-machine direction.

In a preferred embodiment of the present invention, the top sheet comprises a PHA of the present invention.

The topsheet and the backsheet are joined together in any suitable manner. As used herein, the term "joined" encompasses configurations whereby the topsheet is directly joined to the backsheet by affixing the topsheet directly to the backsheet, and configurations whereby the topsheet is indirectly joined to the backsheet by affixing the topsheet to intermediate members which in turn are affixed to the backsheet. In a preferred embodiment, the topsheet and the backsheet are affixed directly to each other in the diaper periphery by attachment means such as an adhesive or any other attachment means known in the art. For example, a uniform, continuous layer of adhesive, a patterned layer of adhesive, or an array of separate lines or spots of adhesive may be used to affix the topsheet to the backsheet.

In a preferred embodiment of the present invention, the adhesive comprises a PHA of the present invention.

Tape tab fasteners are typically applied to the back waistband region of the diaper to provide a fastening means for holding the diaper on the wearer. The tape tab fasteners can be any of those well known in the art, such as the fastening tape disclosed in U.S. Pat. No. 3,848,594 issued to Kenneth B. Buell on Nov. 19, 1974. These tape tab fasteners or other diaper fastening means are typically applied near the corners of the diaper.

Preferred diapers have elastic members disposed adjacent the periphery of the diaper, preferably along each longitudinal edge so that the elastic members tend to draw and hold the diaper against the legs of the wearer. The elastic members are secured to the diaper in an contractible condition so that in a normally unrestrained configuration the elastic members effectively contract or gather the diaper. The elastic members can be secured in an contractible condition in at least two ways. For example, the elastic members may be stretched and secured while the diaper is in an uncontracted condition. Alternatively, the diaper may be contracted, for example, by pleating, an elastic member secured and connected to the diaper while the elastic members are in their relaxed or unstretched condition.

The elastic members may take a multitude of configurations. For example, the width of the elastic members may be varied from about 0.25 mm to about 25 mm or more; the elastic members may comprise a single strand of elastic material or the elastic members may be rectangular or curvilinear. Still further, the elastic members may be affixed to the diaper in any of several ways which are known in the art. For example the elastic members may be ultrasonically bonded, heat and pressure sealed into the diaper using a variety of bonding patterns, or the elastic members may simply be glued to the diaper.

In a preferred embodiment of the present invention, the elastic members comprise a PHA of the present invention.

The absorbent core of the diaper is positioned between the topsheet and backsheet. The absorbent core may be manufactured in a wide variety of sizes and shapes (e.g., rectangular, hour-glass, asymmetrical, etc.) and from a wide variety of materials. The total absorbent capacity of the absorbent core should, however, be compatible with the designed liquid loading for the intended use of the absorbent article or diaper. Further, the size and absorbent capacity of the absorbent core may vary to accommodate wearers ranging from infants through adults.

A preferred embodiment of the diaper has an hour-glass shaped absorbent core. The absorbent core is preferably an absorbent member comprising a web or batt of airfelt, wood pulp fibers, and/or a particulate absorbent polymeric composition disposed therein.

In a preferred embodiment of the present invention, the absorbent polymeric composition of the absorbent core comprises a PHA of the present invention.

Other examples of absorbent articles according to the present invention are sanitary napkins designed to receive and contain vaginal discharges such as menses. Disposable sanitary napkins are designed to be held adjacent to the human body through the agency of a garment, such as an undergarment or a panty or by a specially designed belt. Examples of the kinds of sanitary napkins to which the present invention is readily adapted are shown in U.S. Pat. No. 4,687,478, entitled "Shaped Sanitary Napkin With Flaps" which issued to Kees J. Van Tilburg on Aug. 18, 1987, and in U.S. Pat. No. 4,589,876, entitled "Sanitary Napkin" which issued to Kees J. Van Tilburg on May 20, 1986. It will be apparent that the films of the present invention comprising a PHA of the present invention described herein may be used as the liquid impervious backsheet of such sanitary napkins. On the other hand it will be understood the present invention is not limited to any specific sanitary napkin configuration or structure.

In general, sanitary napkins comprise a liquid impervious backsheet, a liquid pervious topsheet, and an absorbent core placed between the backsheet and the topsheet. The backsheet comprises a PHA of the present invention. The topsheet may comprise any of the topsheet materials discussed with respect to diapers. The adhesives used in may also comprise a PHA of the present invention. The absorbent core may comprise any of the absorbent core materials discussed with respect to diapers, including a PHA of the present invention.

Importantly, the absorbent articles according to the present invention are biodegradable and/or compostable to a greater extent than conventional absorbent articles which employ materials such as a polyolefin (e.g., a polyethylene backsheet.

EXAMPLE 1

Poly(3-hydroxybutyrate-co-3-hydroxyoctanoate)

Poly(3-hydroxybutyrate-co-3-hydroxyoctanoate) is prepared according to the general methods described above and based on the published procedure of Hori et al. (Hori, Y., M. Suzuki, Y. Takahashi, A. Yomaguchi, and T. Nishishita, MACROMOLECULES, Vol. 26, pp. 5533–5534 (1993)) for the polymerization of β-butyrolactone. Specifically, purified [S]- 3-methylpropiolactone ([S]-β-butyrolactone) (9.50 g, 110 mmol) and [S]-3-pentylpropiolactone (0.83 g, 5.8 mmol) are charged into a septum sealed, argon purged, dry, glass tube via syringe. The initiator, 1,3-dichloro- 1,1,3,3-tetrabutyldistannoxane prepared according to R. Okawara and M. Wada, (J. ORGANOMET. CHEM. (1963), Vol. 1, pp. 81–88) and dried overnight in vacuo at 80° C. is dissolved in dry toluene to make a 0.18M solution. Via syringe, 0.65 mL of the initiator solution (0.12 mmol distannoxane) is added to the tube. The tube is gently swirled to mix the contents and then heated at 100° C. for 4 h by immersing its lower half in an oil bath; As the reaction proceeds, the contents of the tube become viscous. After the required time, the tube is removed from the oil bath and allowed to cool to room temperature. The solid is dissolved in chloroform. It is recovered by precipitation into a hexane-ether mixture, collected by filtration, and dried under vacuum. The comonomer composition of the copolymer is determined by $^1$H-NMR spectroscopy and found, within experimental error, to be the same as the charge ratio (95:5). Molecular weight is determined by size exclusion chromatography with chloroform as the mobile phase, and narrow polystyrene standards are used for calibration.

EXAMPLE 2

Poly(3-hydroxybutyrate-co-3-hydroxynonanoate)

Poly(3-hydroxybutyrate-co-3-hydroxynonanoate) is prepared by following the same procedure as in Example 1, with the exception that [S]-3methylpropiolactone (9.50 g, 110 mmol) and [S]-3-hexylpropiolactone (0.91 g, 5.8 mmol) are used as the monomer charge.

EXAMPLE 3

Poly(3-hydroxybutyrate-co-3-hydroxyheptanoate)

Poly(3-hydroxybutyrate-co-3-hydroxyheptanoate) is prepared by following the same procedure as in Example 1, with the exception that [S]-3methylpropiolactone (9.5 g, 110 mmol) and [S]-3-butylpropiolactone (0.74 g, 5.8 mmol) are used as the monomer charge.

EXAMPLE 4

Poly(3-hydroxyvalerate-co-3-hydroxyoctanoate)

Poly(3-hydroxyvalerate-co-3-hydroxyoctanoate) is prepared by following the same procedure as in Example 1, with the exception that [S]-3-ethylpropiolactone (9.50 g, 94.9 mmol) and [S]-3-pentylpropiolactone (0.71 g, 5.0 mmol) are used as the monomer charge.

EXAMPLE 5

Poly(3-hydroxybutyrate-co-3-hydroxydecanoate)

Poly(3-hydroxybutyrate-co-3-hydroxydecanoate) is prepared by following the same procedure described in Example 1, with the exception that [S]-3-methylpropiolactone (9.50 g, 110 mmol) and [S]-3-heptylpropiolactone (0.99 g, 5.8 mmol) are used as the monomer charge.

EXAMPLE 6

Poly(3-hydroxybutyrate-co-3-hydroxydocosanoate)

Poly(3-hydroxybutyrate-co-3-hydroxydocosanoate) is prepared by following the same procedure as in Example 1, with the exception that [S]-3-methylpropiolactone (9.5 g, 110 mmol) and [S]-3-hexadecylpropiolactone (1.96 g, 5.8 mmol) are used as the monomer charge.

EXAMPLE 7

Poly(3-hydroxybutyrate-co-3-hydroxyhexadecanoate)

Poly(3-hydroxybutyrate-co-3-hydroxyhexadecanoate) is prepared by following the same procedure as in Example 1, with the exception that [S]-3-methylpropiolactone (9.5 g, 110 retool) and [S]-3-tridecylpropiolactone (1.48 g, 5.8 retool) are used as the monomer charge.

EXAMPLE 8

Poly(3-hydroxybutyrate-co-3-hydroxyvalerate-co-3-hydroxyoctanoate)

Poly(3-hydroxybutyrate-co-3-hydroxyvalerate-co-3-hydroxyoctanoate) is prepared by following the same procedure as in Example 1, with the exception that [S]-3-methylpropiolactone (7.20 g, 83.6 mmol), [S]-3-ethylpropiolactone (1.14 g, 11.4 mmol), and [S]-3pentylpropiolactone (0.71 g, 5.0 retool) are used as the monomer charge.

EXAMPLE 9

Poly(3-hydroxybutyrateoco-3-hydroxyoctanoate-co-3-hydroxydecanoate)

Poly(3-hydroxybutyrateoco-3-hydroxyoctanoate-co-3-hydroxydecanoate) is prepared by following the same procedure as in Example 1, with the exception that [S]-3-methylpropiolactone (9.50 g, 110 mmol), [S]-3-pentylpropiolactone (0.41 g, 2.9 retool), and [S]-3-heptylpropiolactone (0.50 g, 2.9 mmol) are used as the monomer charge.

EXAMPLE 10

Poly(3-hydroxybutyrate-co-3-hydroxyvalerate-co-3-hydroxyoctanoate-co-3-hydroxydecanoate)

Poly(3-hydroxybutyrate-co-3-hydroxyvalerate-co-3-hydroxyoctanoate-co-3-hydroxydecanoate) is prepared by following the same procedure as in Example 1, with the exception that [S]-3-methylpropiolactone (7.20 g, 83.6 mmol), [S]-3-ethylpropiolactone (1.14 g, 11.4 mmol), [S]-3-pentylpropiolactone (0.36 g, 2.5 retool), and [S]-3-heptylpropiolactone (0.43 g, 2.5 mmol) are used as the monomer charge.

EXAMPLE 11

Compostable Single Layer Film

Poly(3-hydroxybutyrate-co-3-hydroxyoctanoate) (PHB-O) of composition 5 mole % octanoate/95 mole % butyrate is introduced into a single screw extruder (Rheomix Model 202) with screw diameter of 0.75 inch. A constant taper screw having 20:1 length to diameter ratio and a 3:1 compression ratio is employed. The temperature of both heating zones of the extruder barrel is 25° C. above the melt temperature of the PHB-O. The extruder is equipped with a die of width 6 inch and a die gap of 0.04 inch. The die is maintained at 20° C. above the melt temperature of the PHB-O. The copolymer is melted within the extruder and pumped to the die at the other end of the extruder, The screw rpm is kept constant at 30 rpm. The copolymer is forced through the die and is collected on a take-up roll collection system (Postex) at a rate that allows crystallization of the polymer before take-up. The width of these films are nominally 4 inch and the thickness are approximately 0.002 inch.

EXAMPLE 12

Compostable Single Layer Film

Films of PHB-O (95:5) are made by melting the material between Teflon sheets in a Carver Press (Fred S. Carver Inc., Menomonee Falls, Wis.) at 20° C. above the melt temperature. Pressure on the sheets are adjusted to produce films of approximately 0.25 mm thick. The films are then identically cooled to room temperature by placing the molds between large (5 kg) aluminum plates and allowing the films to cool to room temperature.

EXAMPLE 13

Compostable Multilayer Film

Sheets of PHB-O film may be prepared as in Example 11 of compositions PHB-O (95:5) and PHB-O (50:50). These sheets may then encase a sheet of a polymer with good oxygen barrier properties but a poor water vapor transmission rate, or a polymer film that may be water soluble such a poly(vinyl alcohol) (PVA). The films are placed in carver press stacked in the following order PHB-0(95:5), PHB-0(50:50), PVA, PHB-O (50:50), PHB-O(95:5). The material is then pressed at a temperature 5° C. above the melt temperature of PHB-O(50:50), but still below the melting temperature of the PHB-O(95:5). After compression at 2000 lb for 30 min, the pressure is released and the film is allowed to cool to room temperature.

EXAMPLE 14

Compostable Disposable Diaper

A disposable baby diaper according to this invention is prepared as follows. The dimensions listed are for a diaper intended for use with a child in the 6–10 kilogram size range. These dimensions can be modified proportionately for different size children, or for adult incontinence briefs, according to standard practice.

1. Backsheet: 0.020 - 0.038 mm film consisting of a 92:8 poly(3-hydroxybutyrate-co-hydroxyoctanoate) copolymer (prepared as described in Example 1 ); width at top and bottom 33 cm; notched inwardly on both sides to a width-at-center of 28.5 cm; length 50.2 cm.

2. Topsheet: carded and thermally bonded staple-length polypropylene fibers (Hercules type 151 polypropylene); width at top and bottom 33 cm; notched inwardly on both sides to a width-at-center of 28.5 cm; length 50.2 cm.

3. Absorbent core: comprises 28.6 g of cellulose wood pulp and 4.9 g of absorbent gelling material particles (commercial polyacrylate from Nippon Shokubai); 8.4 mm thick, calendered; width at top and bottom 28.6 cm; notched inwardly at both sides to a width-at-center of 10.2 cm; length 44.5 cm.

4. Elastic leg bands: four individual rubber strips (2 per side); width 4.77 mm; length 370 mm; thickness 0.178 mm (all the foregoing dimensions being in the relaxed state).

The diaper is prepared in standard fashion by positioning the core material covered with the topsheet on the backsheet and gluing.

The elastic bands (designated "inner" and "outer", corresponding to the bands closest to, and farthest from, the core, respectively) are stretched to ca. 50.2 cm and positioned between the topsheet/backsheet along each longitudinal side (2 bands per side) of the core. The inner bands along each side are positioned ca. 55 mm from the narrowest width of the core (measured from the inner edge of the elastic bank). This provides a spacing element along each side of the diaper comprising the flexible topsheet/backsheet material between the inner elastic and the curved edge of the core. The inner bands are glued down along their length in the stretched state. The outer bands are positioned ca. 13 mm from the inner bands, and are glued down along their length in the stretched state. The topsheet/backsheet assembly is flexible, and the glued-down bands contract to elasticize the sides of the diaper.

EXAMPLE 15

Compostable Lightweight Pantiliner

A lightweight pantiliner suitable for use between menstrual periods comprises a pad (surface area 117 $cm^2$; SSK air felt 3.0 g) containing 1.0 g of absorbent gelling material particles (commercial polyacrylate; Nippon Shokubai); said pad being interposed between a porous formed-film topsheet according to U.S. Pat. No. 4,463,045 and a backsheet which comprises a 0.03 mm thickness 92:8 poly(3-hydroxybutyrate-co-hydroxyoctanoate) copolymer film, as prepared in accordance with Example 1.

EXAMPLE 16

Compostable Sanitary Napkin

A catamenial product in the form of a sanitary napkin having two flaps extending outward from its absorbent core is prepared using a pad in the manner of Example 15

(surface area 117 cm$^{2;\ 8.5}$ g SSK air felt), per the design of U.S. Pat. No. 4,687,478, Van Tillburg, Aug. 18, 1987. The backsheet and topsheet materials are the same as described in Example 15.

EXAMPLE 17

Compostable Disposable Diaper

The diaper of Example 14 is modified by replacing the backsheet with a backsheet consisting of a 0.020 to 0.038 mm thickness film comprising a 92:8 poly(3-hydroxybutyrate-co-hydroxydecanoate) copolymer film (prepared as described in Example 5).

EXAMPLE 18

Compostable Sheet

The film preparation procedure of Example 11 is modified by replacing the die on the extruder with a slot die of thickness approximately 0.25 cm and width 15 cm. Take-up after extrusion is accomplished by inserting the sheet emerging from the extruder between two counter-rotating cylinders. The sheet is drawn from the extruder in this manner and cut in lengths of 32 cm. Sheets of approximately 13 cm wide and 0.18 cm thick are obtained.

EXAMPLE 19

Compostable Fiber

PHB-O of composition 5 mole% octanoate/95 mole% butyrate is introduced into a single screw extruder (Rheomix Model 202) with screw diameter of 0.75 inch. A constant taper screw having 20:1 length to diameter ratio and a 3:1 compression ratio is employed. The temperature of both heating zones of the extruder barrel is 25° C. above the melt temperature of the PHB-O. The extruder is equipped with a nozzle die containing 5 orifices of diameter 500 min. The die is maintained:at 20° C. above the melt temperature of the PHB-O. The polymer is melted within the extruder and pumped to the die at the other end of the extruder. The screw rpm is kept constant at 30 rpm. The polymer is forced through the die and the melted extruded fibers are lead through a region where a rapid air stream is applied such that the polymer fibers elongates and thins to approximately one fifth of the diameter of the orifices (ca. 100 mm). The fibers are collected on a cardboard mat. A wide distribution of fiber lengths are obtained up several cm in length. Most fiber lengths (over 50%) are in the range of 1.3 to 15 cm.

EXAMPLE 20

Compostable Rigid Foam

PHB-O (40 g) of composition 5 mole % octanoate/95 mole % butyrate and 4 g of a common blowing agent, p,p'-oxy-bis benzenesulphonhydrazide are charged to the mixing chamber of a Rheomix type 600 melt blender equipped with roller blades. The mixing chamber temperature is heated above the melting temperature of PHB-O, but below the degradation temperature of the blowing agent (158° C.). After mixing for 10 minutes at 60 rpm, the copolymer mixture is collected and is transferred to a heated aluminum pan, spread about so that the resulting mass is about 0.5 cm in thickness. The copolymer is then place in an oven (National Appliance Company, model 5830) and heated to the PHB-O melt temperature again, and is held at that temperature until the copolymer is completely molten (ca. 5 min). The oven temperature is then raised to 160° C. at which temperature the blowing agent degrades and copolymer begins foaming. At this point the copolymer foam is removed from the oven and is placed into a second oven at a temperature of the maximum crystallization rate of the PHB-O (about 80° C.). The copolymer is left in this oven for 6 hours.

EXAMPLE 21

Compostable Flexible Foam

The procedure of Example 20 is used with the following modifications: 40 g of Poly(3-hydroxybutyrate-co-3-hydroxyoctanoate) of composition 60 mote% octanoate/40 mole % butyrate (PHB-O (40:60)) is used in place of PHB-O (95:5).

EXAMPLE 22

Compostable Molded Article

Injection molded articles are obtained by using a Mini Max Molder model CS-183 (Custom Scientific Instruments, Whippeny, N.J.). The temperature of the rotor and strator cup is held constant at 20° C. above the melt temperature of the polyhydroxyalkanoate used. About 0.5 grams of PHB-O (95:5) is charged to the stator cup and allowed to melt for 3 minutes. The molten copolymer is radially mixed by raising and lowering the rotor tip five times. A dumbbell-shaped steel mold is sprayed with a light coating of mold silicone release agent. The mold is placed on the mold support wheel of the Mini Max Molder and the molten polymer is injected into the mold by action of the rotor tip. The copolymer is molded into a dumbbell shaped pieces 0.03 inch thick, I inch long, 0.125 inch wide at the middle of the piece and 0.25 inch wide at the ends. These molded pans are suitable for mechanical testing.

EXAMPLE 23

Compostable Nonwoven Fabric

Poly(3-hydroxybutyrate-co-3-hydroxyoctanoate) (PHB-O) of composition 2 mole % octanoate/98 mole % butyrate is introduced into a single screw extruder (Rheomix Model 202, Paramus, N.J.) with screw diameter of 0.75 inch. A constant taper screw having 20:1 length to diameter ratio and a 3:1 compression ratio is employed. The temperature of both heating zones of the extruder barrel is 25° C. above the melt temperature of the PHB-O. The extruder is equipped with a nozzle die containing 5 orifices of diameter 500 min. The die is maintained at 20° C. above the melt temperature of the PHB-O. The polymer is melted within the extruder and pumped to the die at the other end of the extruder. The screw rpm is kept constant at 30 rpm. The polymer is forced through the die and the melted extruded fibers are lead through a region where a rapid air stream is applied such that the polymer fibers elongates and thins to approximately one fifth of the diameter of the orifices (ca. 100 mm). The fibers are collected on a cardboard mat. The mat is moved in a fashion so that a 10 cm×10 cm area is covered uniformly with fibers. Collection of fibers on the mat continues, until there is approximately 0.5 cm thick fiber mat. A wide distribution of fiber lengths are obtained up several inches in length. Most fiber lengths (over 50%) are in the range of 0.5 to 6 inches. The mat is then transferred to a Carver Press (Fred S. Carver Inc., Menomonee Falls, Wis.) and pressed at a 1000 lb force for 10 minutes at temperature 5° C. below the melting temperature of the PHB-O. The resulting nonwoven sheet is removed from the press.

EXAMPLE 24

Compostable Elastomer

Films of PHB-O (70:30) are made by melting the material between Teflon sheets in a at 20° C. above the melt temperature. Pressure on the sheets is adjusted to produce films of approximately 0.5 mm thick. The films are then identically cooled to room temperature by placing the molds between large (5 kg) aluminum plates and allowing the films to cool to room temperature. The films are aged for 2 days, then subsequently cut into strips 10 cm long and 1 cm wide. The strips am then placed in an instron universal testing machine (Model 1122, Canton, Mass.) and are elongated at a rate of 1 in/min until 300% elongation of the original length is achieved. The films are held elongated for two days until crystallinity develops further. The strips are removed from the Instron and upon subsequent extension, the material returns to its former (post Instron treatment) length.

EXAMPLE 25

Compostable Adhesive

PHB-O (50:50) may be used as a hot-melt adhesive in the following manner. About 1 g of PHB-O (50:50) is placed between two polymer films, such as poly(vinyl alcohol) (PVA), or poly(3-hydroxybutyrate) (PHB) or any other PHA which has a melting temperature at least 10° C. higher than PHB-O (50:50). The films/adhesive assembly is placed in a Carver Press (Fred S. Carver Inc., Menomonee Falls, Wis.) and is then pressed at a temperature 5° C. above the melt temperature of PHO:B (50:50). After compression at 2000 lb force for 30 min, the pressure is released and the bonded film assembly is allowed to cool to room temperature.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. An absorbent article comprising:

a) a liquid pervious topsheet;

b) a liquid impervious backsheet comprising a biodegradable copolymer, wherein the biodegradable copolymer comprises at least two randomly repeating monomer units wherein the first randomly repeating monomer unit has the structure

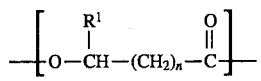

wherein $R^1$ is H, or $C_1$ or $C_2$ alkyl, and n is 1 or 2; the second randomly repeating monomer unit has the structure

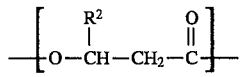

wherein $R^2$ is a $C_4$–$C_{19}$ alkyl or alkenyl; and wherein at least 50% of the randomly repeating monomer units have the structure of the first randomly repeating monomer unit; and c) an absorbent core positioned between the topsheet and the backsheet.

2. The absorbent article of claim 1 wherein the biodegradable copolymer comprises one or more additional randomly repeating monomer units having the structure

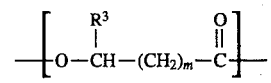

wherein $R^3$ is H, or a $C_1$–$C_{19}$ alkyl or alkenyl; and m is 1 or 2; and wherein the additional randomly repeating monomer units are not the same as the first randomly repeating monomer unit or the second randomly repeating monomer unit.

3. The absorbent article of claim 1, in the form of a disposable diaper, sanitary napkin, or pantiliner.

4. The absorbent article of claim 1, wherein the liquid pervious topsheet comprises a biodegradable copolymer, wherein the biodegradable copolymer comprises at least two randomly repeating monomer units wherein the first randomly repeating monomer unit has the structure

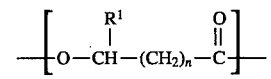

wherein $R^1$ is H, or $C_1$ or $C_2$ alkyl, and n is 1 or 2; the second randomly repeating monomer unit has the structure

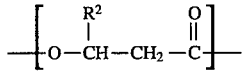

wherein $R^2$ is a $C_4$–$C_{19}$ alkyl or alkenyl; and wherein at least 50% of the randomly repeating monomer units have the structure of the first randomly repeating monomer unit.

5. The absorbent article of claim 1, wherein the absorbent article additionally comprises one or more elastic members disposed adjacent to the periphery of the diaper, wherein the elastic member comprises a biodegradable copolymer, wherein the biodegradable copolymer comprises at least two randomly repeating monomer units wherein the first monomer unit has the structure

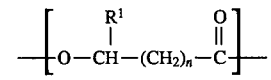

wherein $R^1$ is H, or $C_1$ or $C_2$ alkyl, and n is 1 or 2; the second randomly repeating monomer unit has the structure

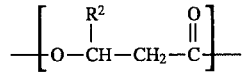

wherein $R^2$ is a $C_4$–$C_{19}$ alkyl or alkenyl; and wherein at least 50% of the randomly repeating monomer units have the structure of the first randomly repeating monomer unit.

* * * * *